US011365246B2

(12) United States Patent
Mor

(10) Patent No.: US 11,365,246 B2
(45) Date of Patent: Jun. 21, 2022

(54) ANTI CCL24 (EOTAXIN2) ANTIBODIES FOR USE IN THE TREATMENT OF HEPATIC DISEASES

(71) Applicant: CHEMOMAB LTD., Tel Aviv (IL)

(72) Inventor: Adi Mor, Tel Aviv (IL)

(73) Assignee: CHEMOMAB LTD., Tel Aviv (IL)

( * ) Notice: Subject to any disclaimer, the term of this patent is extended or adjusted under 35 U.S.C. 154(b) by 237 days.

(21) Appl. No.: 16/492,026

(22) PCT Filed: Mar. 8, 2018

(86) PCT No.: PCT/IL2018/050276
§ 371 (c)(1),
(2) Date: Sep. 6, 2019

(87) PCT Pub. No.: WO2018/163185
PCT Pub. Date: Sep. 13, 2018

(65) Prior Publication Data
US 2020/0040070 A1 Feb. 6, 2020

(30) Foreign Application Priority Data
Mar. 8, 2017 (IL) .......................................... 251024

(51) Int. Cl.
| | |
|---|---|
| C07K 16/24 | (2006.01) |
| A61P 1/16 | (2006.01) |
| A61K 39/395 | (2006.01) |
| A61K 45/06 | (2006.01) |
| A61K 39/00 | (2006.01) |

(52) U.S. Cl.
CPC .......... *C07K 16/24* (2013.01); *A61K 39/3955* (2013.01); *A61K 45/06* (2013.01); *A61P 1/16* (2018.01); *A61K 2039/505* (2013.01); *C07K 2317/24* (2013.01); *C07K 2317/565* (2013.01); *C07K 2317/76* (2013.01); *C07K 2317/92* (2013.01)

(58) Field of Classification Search
CPC ................ C07K 16/24; C07K 2317/24; C07K 2317/565; C07K 2317/76; C07K 2317/92; A61K 45/06; A61K 2039/505; A61P 1/16
See application file for complete search history.

(56) References Cited

FOREIGN PATENT DOCUMENTS

| | | |
|---|---|---|
| WO | 2010/086854 A1 | 8/2010 |
| WO | 2015/132790 A2 | 9/2015 |

OTHER PUBLICATIONS

Brown et al., Tolerance of single, but not multiple, amino acid replacements in antibody VH CDR 2: a means of minimizing B cell wastage from somatic hypermutation? J. Immunology 156: 3285-3291, 1996.*
Vajdos et al., Comprehensive functional maps of the antigen-binding site of an anti-ErbB2 antibody obtained with shotgun scanning mutagenesis. J. Mol. Biol. 320:415-428, 2002.*
Segal-Salto et al., A blocking monoclonal antibody to CCL24 alleviates liver fibrosis and inflammation in experimental models of liver damage. JHEP Rep. Jan. 2, 2020;2(1):100064, pp. 1-10.*
Ablin et al., "Protective effect of eotaxin-2 inhibition in adjuvant-induced arthritis", Clinical & Experimental Immunology, 2010, vol. 161, No. 2, pp. 276-283.
Bataller et al., "Liver fibrosis", The Journal of Clinical Investigation, 2005, vol. 115, No. 2, pp. 209-218, XP002450194.
Ben-Ari et al., "CM-101 a novel CCL24 blocking monoclonal antibody ameliorates hepatic injury in NASH induced mouse model", Conference Reports for NATAP, 2017, XP055472939—retrieved online at www.natap.org/2017/AASLD/AASLD_123.htm.
Fiorucci et al., "Cross-Talk between Farnesoid-X-Receptor (FXR) and Peroxisome Proliferator-Activated Receptor gamma Contributes to the Antifibrotic Activity of FXR Ligands in Rodent Models of Liver Cirrhosis", The Journal of Pharmacology and Experimental Therapeutics, 2005, vol. 315, No. 1, pp. 58-68, XP008060972.
Friedman, "Liver fibrosis—from bench to bedside", Journal of Hepatology, 2003, vol. 38, pp. 38-53, XP055048466.
Jin et al., "CCL24 contributes to HCC malignancy via RhoB-VEGFA-VEGFR2 angiogenesis pathway and indicates poor prognosis", Oncotarget, 2017, vol. 8, No. 3, pp. 5145-5146, XP055472928.
Maor et al., "Expression of the chemokine CCL24 and its receptor in the sera and livers of patients with non-alcoholic fatty liver disease", Journal of Hepatology, 2018, vol. 68, p. S341, XP055472935.
Mausner-Fainberg et al., "Eotaxin-2 blockade ameliorates experimental autoimmune encephalomyelitis", World J. Immunol., 2013, vol. 3, No. 1, pp. 7-14.
Mor et al., "Anti eotaxin-2 antibodies attenuate the initiation and progression of experimental atherosclerosis", WJCD, 2013, vol. 3, No. 4, pp. 339-346.
Segal et al., "A novel CCL24 blocking monoclonal antibody ameliorates liver injury in experimental models of cholestasis", Journal of Hepatology, 2018, pp. S451-S452, XP055472934.

* cited by examiner

*Primary Examiner* — Ruixiang Li
(74) *Attorney, Agent, or Firm* — Vorys, Sater, Seymour and Pease LLP; William L. Klima

(57) ABSTRACT

Provided concerns isolated anti CCL24 (eotaxin 2) antibodies for method of treatment of hepatic pathologies.

4 Claims, 15 Drawing Sheets
Specification includes a Sequence Listing.

Fig. 3D
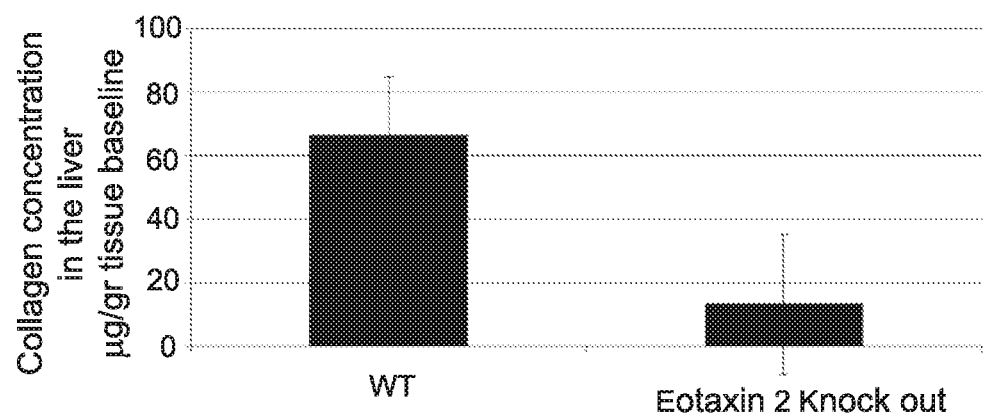
Fig. 3E
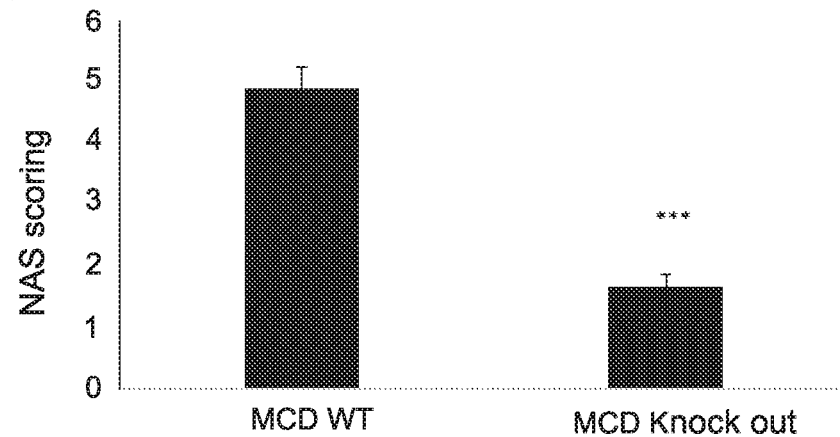
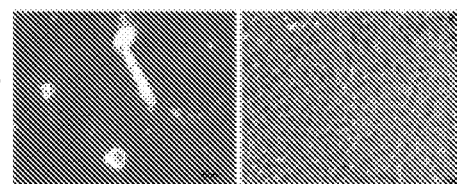
Fig. 3F Normal diet, WT — Fig. 3G
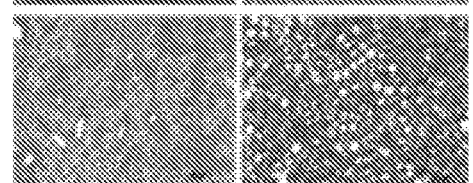
Fig. 3H MCD diet, WT — Fig. 3I
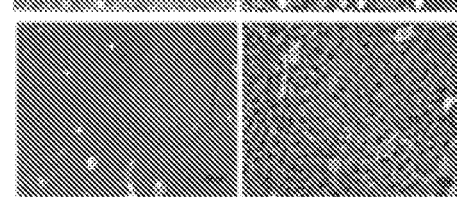
Fig. 3J MCD diet, Knockout — Fig. 3K

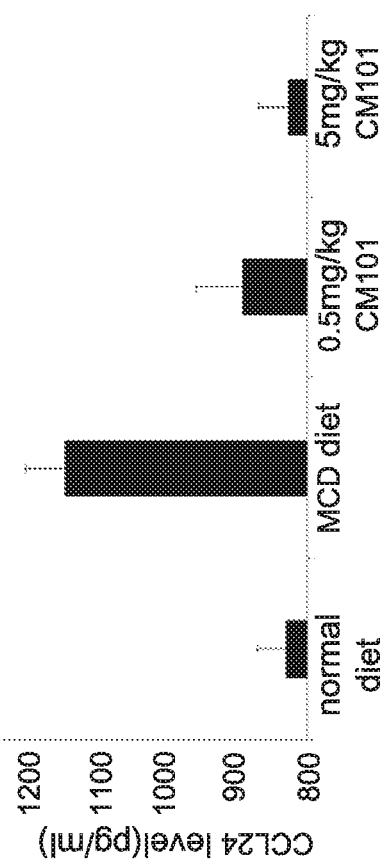
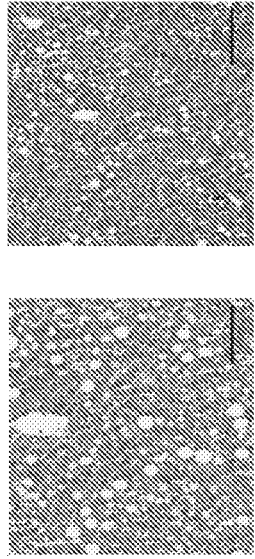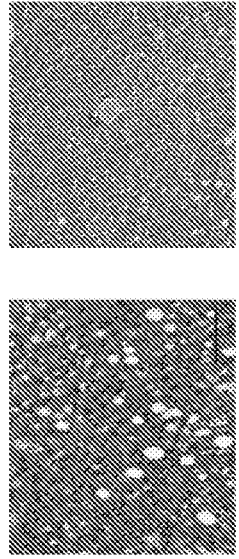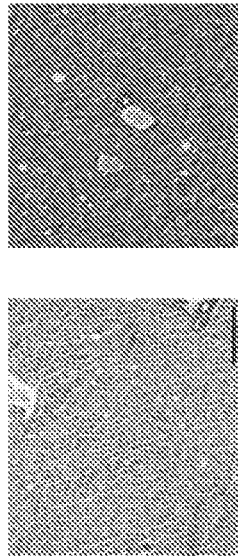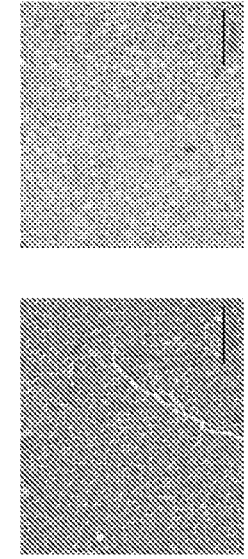

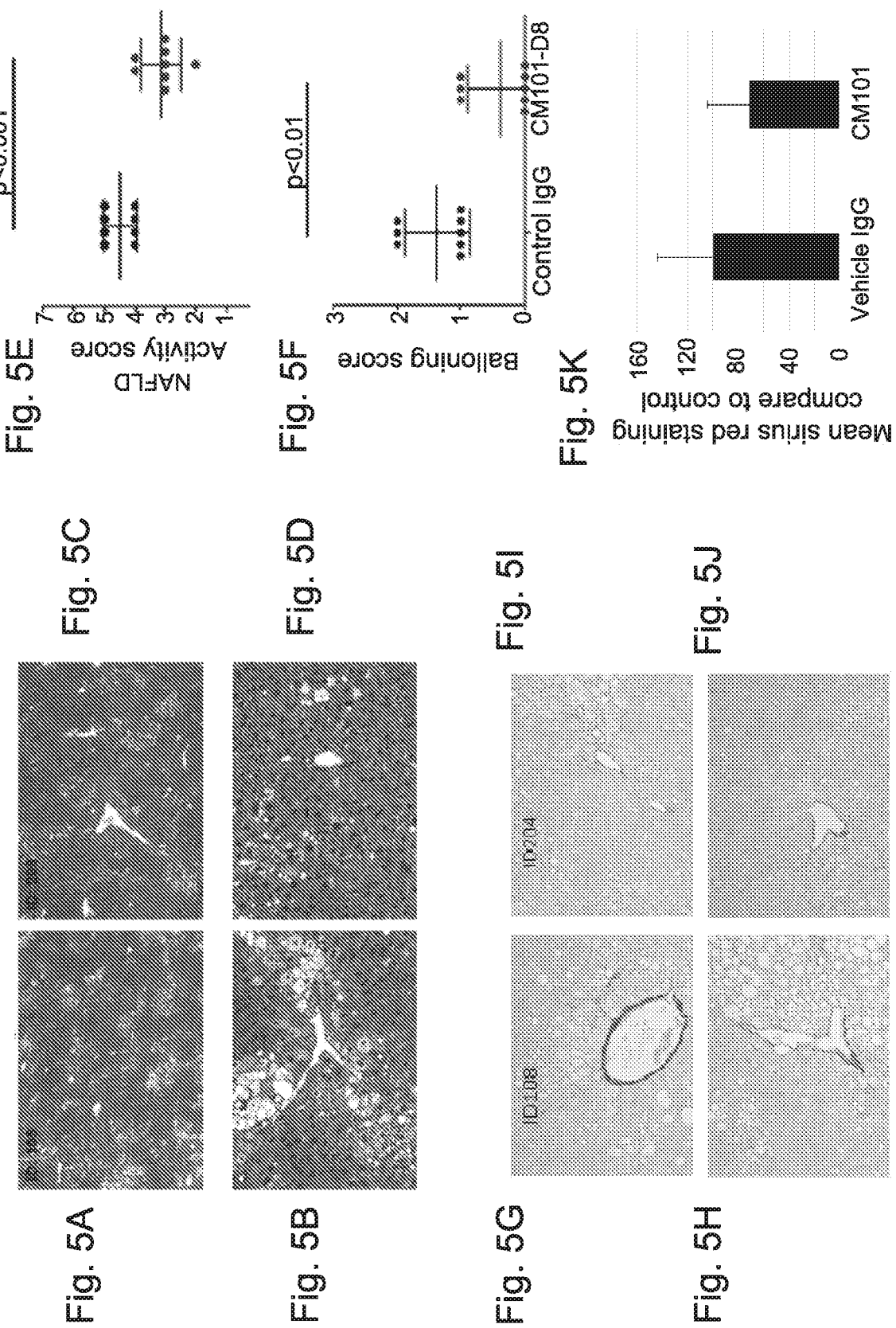

Fig. 5L 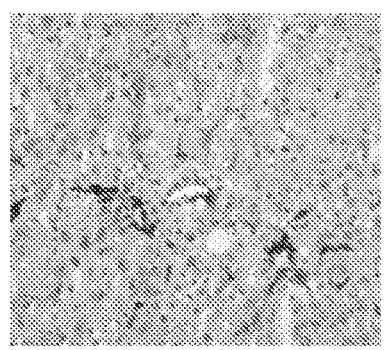 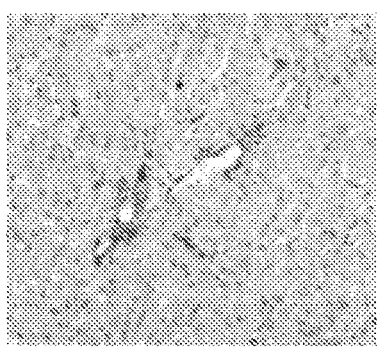 Fig. 5M
α-SMA

Fig. 6A 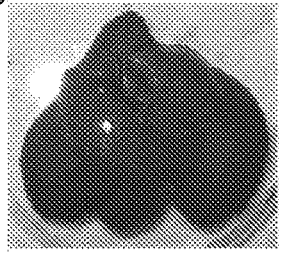 Fig. 6D 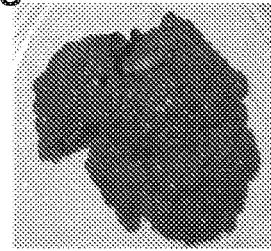 Fig. 6G 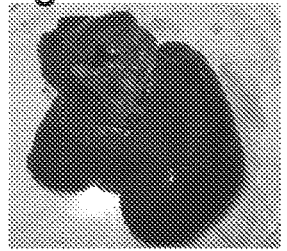
Fig. 6B 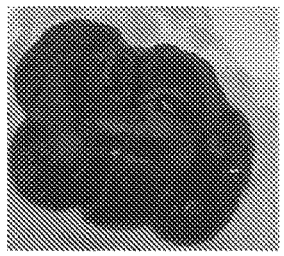 Fig. 6E 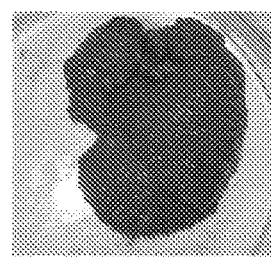 Fig. 6H 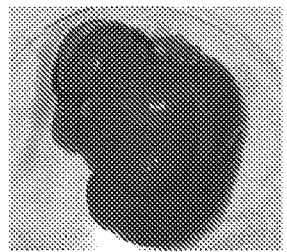
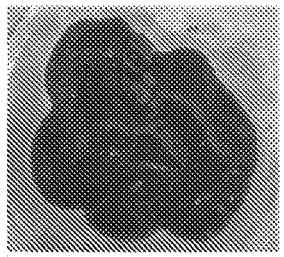 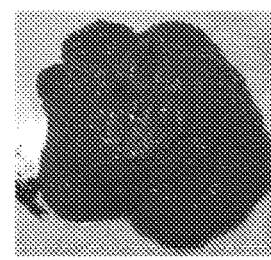 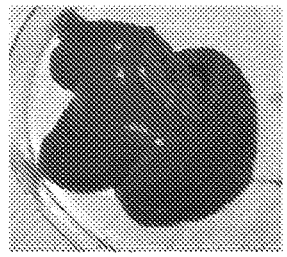
Fig. 6C Fig. 6F Fig. 6I

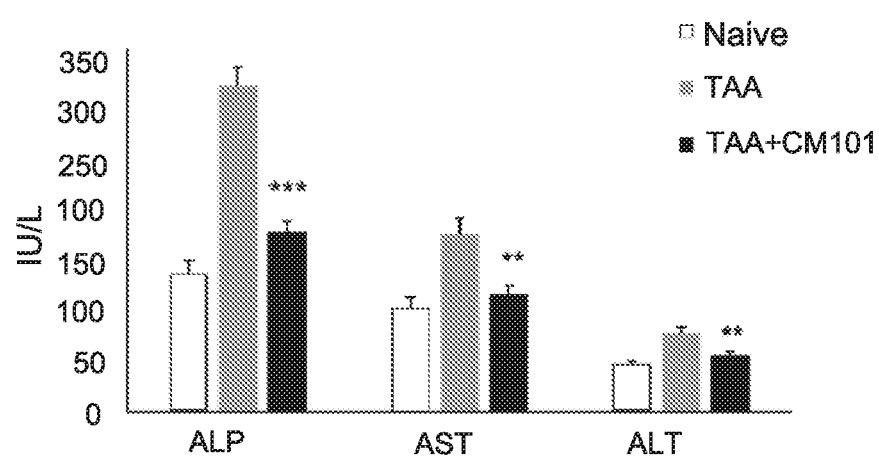
Fig. 6J
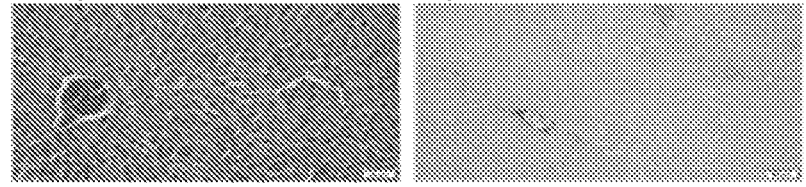
Fig. 6K   Fig. 6L
Naive
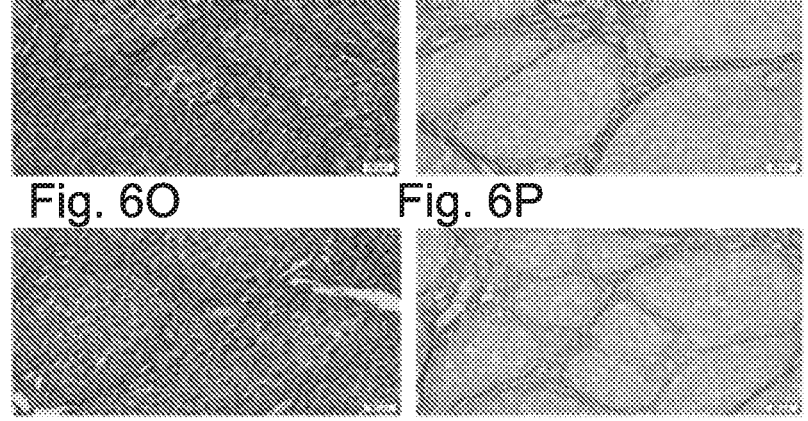
Fig. 6M   Fig. 6N
Fig. 6O   Fig. 6P
TAA
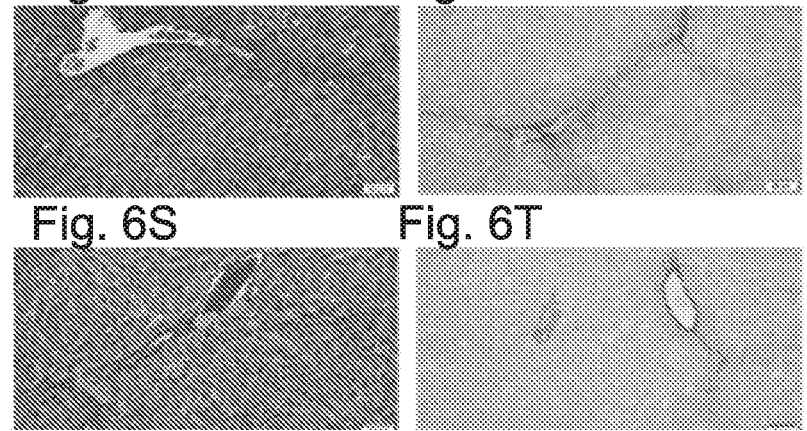
Fig. 6Q   Fig. 6R
Fig. 6S   Fig. 6T
TAA+CM101

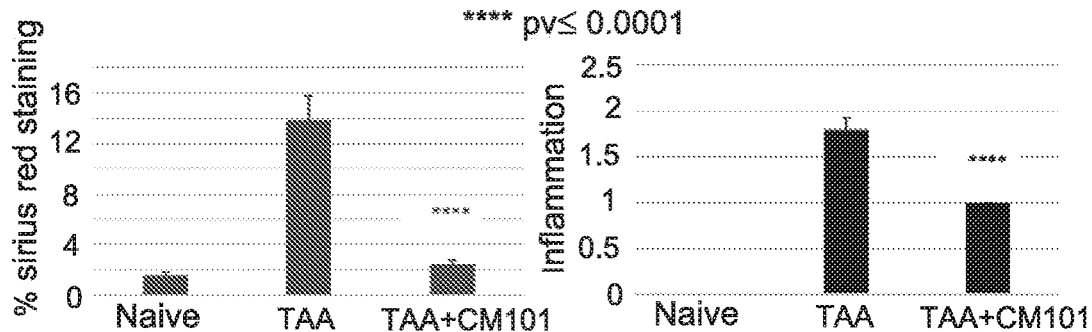
Fig. 6U      Fig. 6V
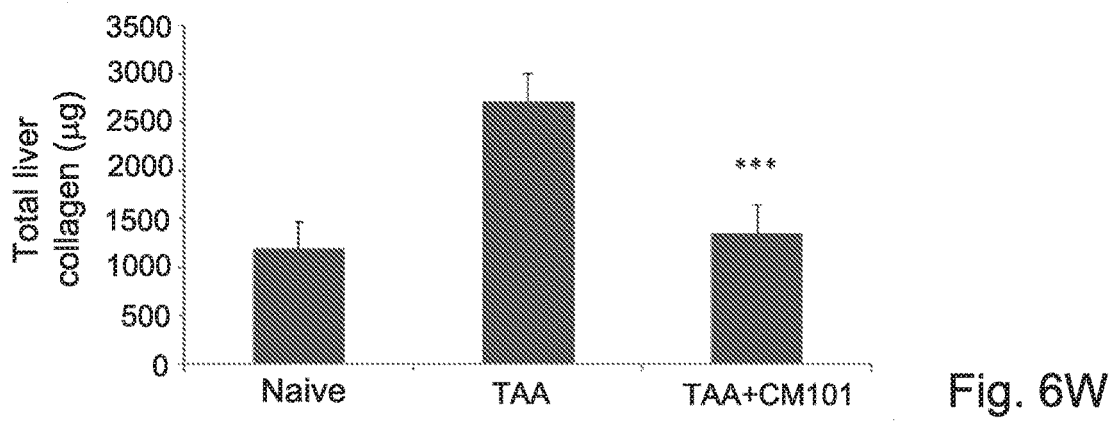
Fig. 6W
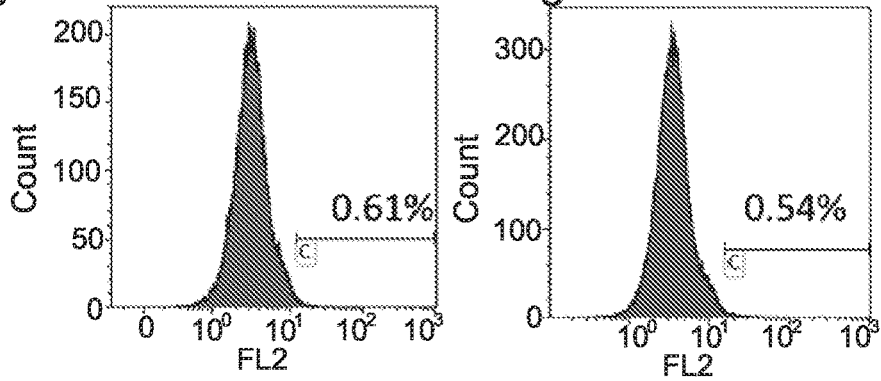
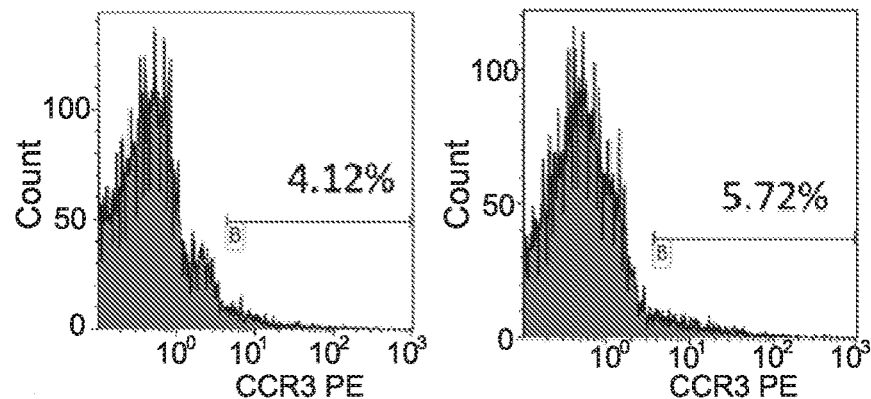

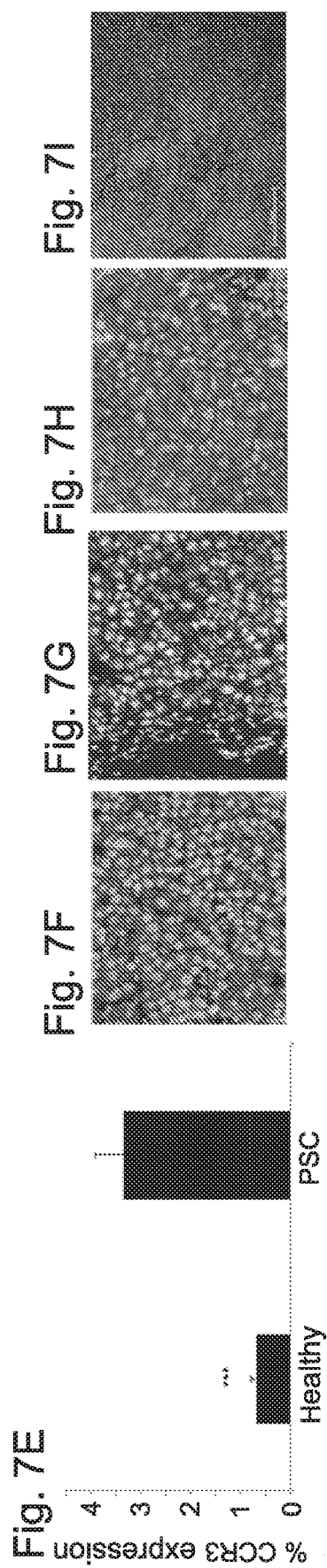
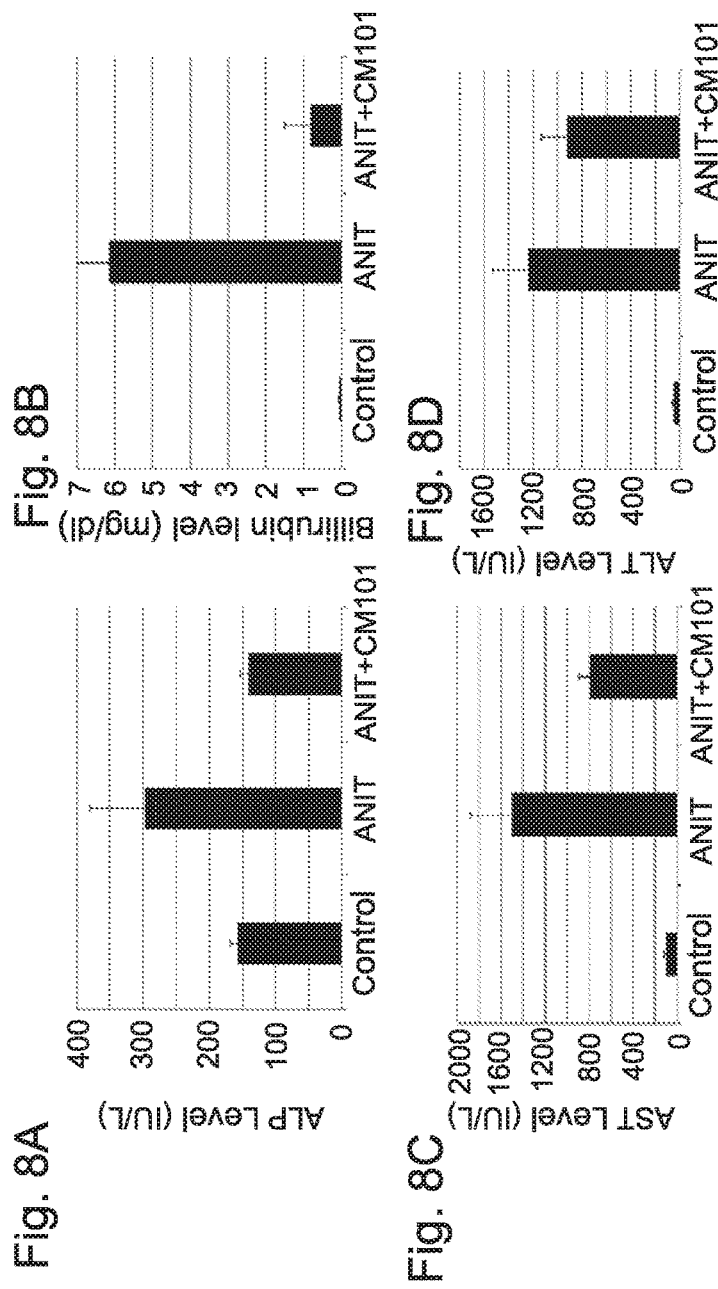

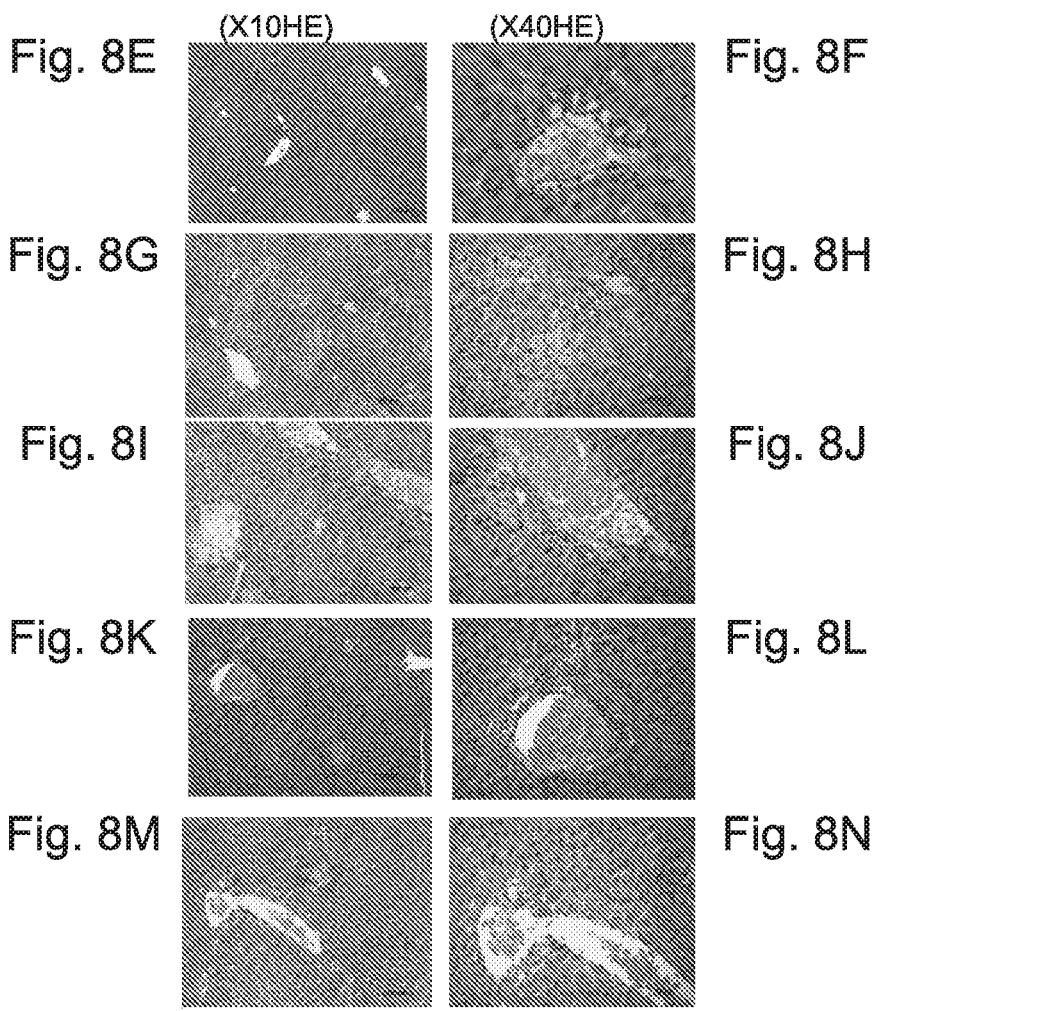
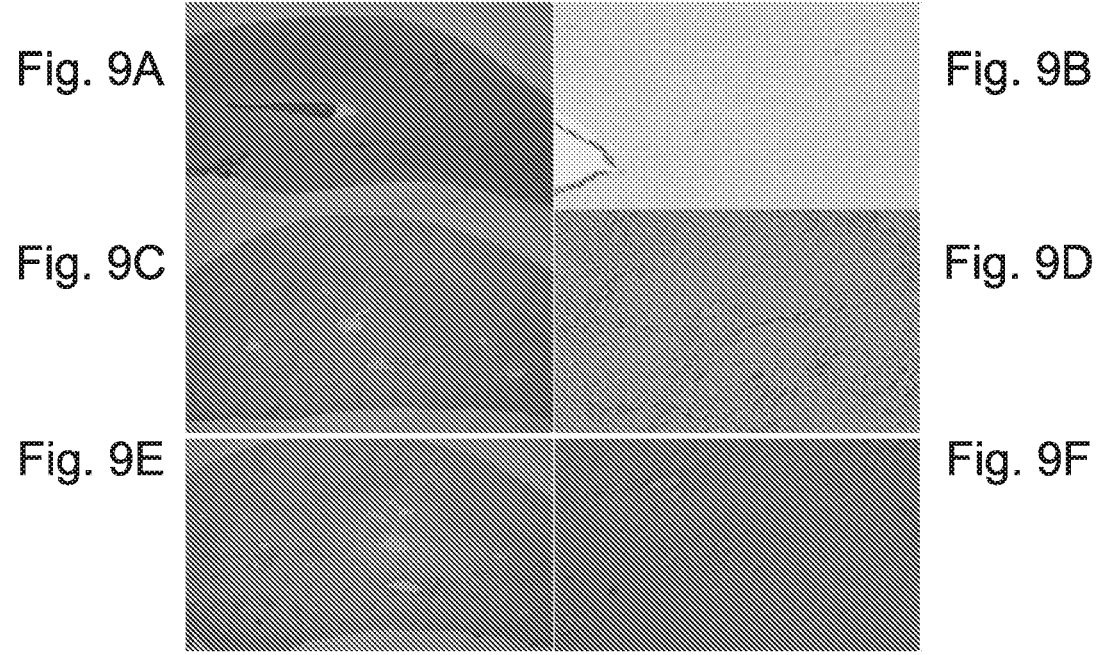

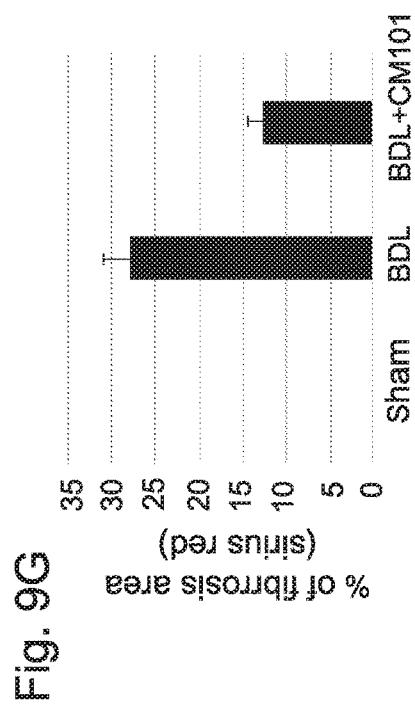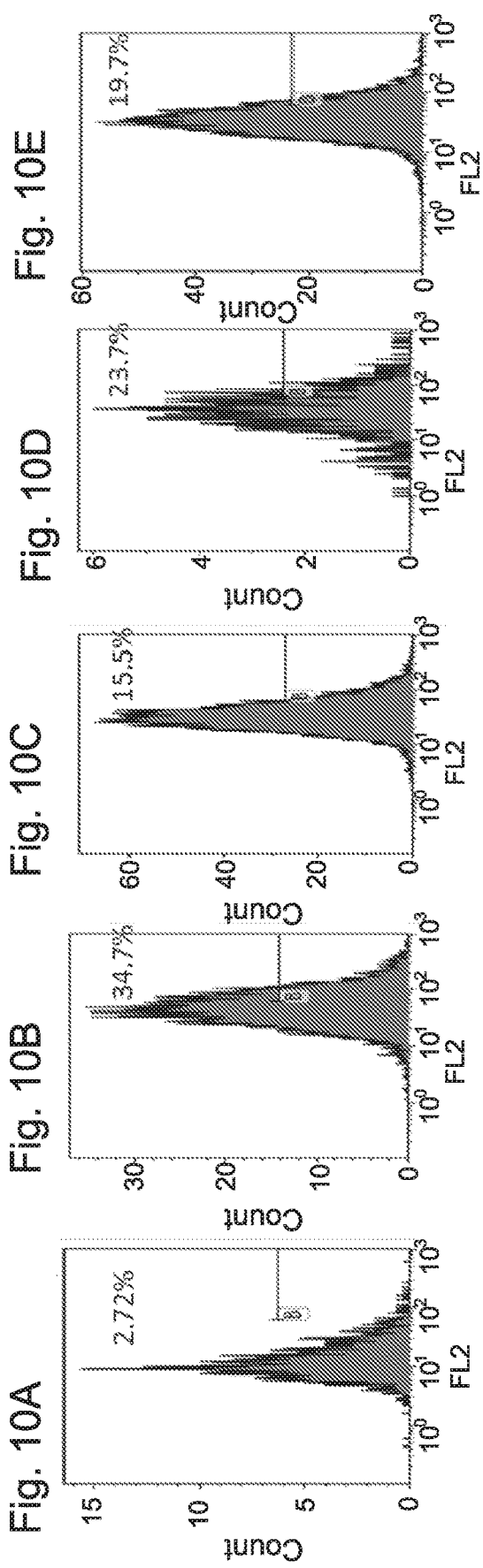

ANTI CCL24 (EOTAXIN2) ANTIBODIES FOR USE IN THE TREATMENT OF HEPATIC DISEASES

SEQUENCE LISTING

The Sequence Listing submitted in text format (.txt) filed on Sep. 6, 2019, named "SequenceListing.txt", created on Sep. 6, 2019 (9.19 KB), is incorporated herein by reference.

TECHNOLOGICAL FIELD

The present invention concerns the use of anti CCL24 (eotaxin2) monoclonal antibodies in the treatment of hepatic diseases.

BACKGROUND

Chemokine (C-C motif) ligand 24 (CCL24 or eotaxin2) is a chemokine that promotes cell trafficking and regulates inflammatory activities through the C-C chemokine receptor type 3 (CCR3) complex, especially by inducing chemotaxis of eosinophils, fibroblasts and T-cells. CCL24 is produced by several inflammatory cells and its receptor CCR3 is present on eosinophils, T-cells, monocytes and fibroblasts.

CCL24 is known to be involved in allergy conditions as there is a significant increase in the levels of CCL24 during the allergic response.

WO 2010/086854 discloses antibodies directed against CCL24 that were effective in animal models of cardiovascular, autoimmune and inflammatory diseases.

Mor et al (2013 WJCD. Vol. 3 No. 4: 339-346) show that a monoclonal antibody prepared against CCL24 attenuated adhesion of lymphocytes to fibronectin and potently inhibited their migration towards vascular endothelial growth factor (VEGF). The antibodies also significantly reduced atherosclerotic plaques in Apolipoprotein E (ApoE) knockout mice. As described in Ablin et al. (2010; V161(2):276-83) and Mausner et al. (World J. Immunol. 2013 March; 3(1):7-14) inhibition of CCL24 demonstrated a protective effect in a rat model of Rheumatoid arthritis and in a mouse model of experimental autoimmune encephalomyelitis.

WO 2015/132790 discloses isolated polyspecific antibodies directed to a unique epitope in the chemokine CCL24, whereby the antibodies bind additional CCR3-binding chemokines. These antibodies were shown to be effective in inhibiting fibrotic and inflammatory features in murine models of systemic sclerosis and idiopathic pulmonary fibrosis (IPF).

Lei Jin et al (2017 Oncotarget, Vol. 8 (no. 3): 5135-5148) show that CCL24 contributes to hepatocellular carcinoma (HCC) via RhoB-VEGFA-VEGFR2 angiogenesis and indicates poor prognosis. However, the involvement of CCL24 in hepatic pathologies such as hepatitis, non-alcoholic fatty liver disease (NAFLD, including nonalcoholic fatty liver (NAFL), cholestasis and intrahepatic cholestatic liver diseases such as primary sclerosing cholangitis (PSC) and primary biliary cirrhosis (PBC) was not demonstrated previously.

GENERAL DESCRIPTION

The present invention therefore provides in a first of its aspects an isolated anti CCL24 (eotaxin2) antibody, or any antigen-binding fragment thereof, for use in the treatment of hepatic pathologies.

In one embodiment said hepatic pathologies are selected from the group consisting of non-alcoholic fatty liver diseases (NAFLD), cholestasis, intrahepatic cholestatic liver diseases, hepatitis (e.g. alcoholic hepatitis) and liver cirrhosis.

In one embodiment, said NAFLD is nonalcoholic fatty liver (NAFL) or nonalcoholic steatohepatitis (NASH).

In one embodiment, said hepatic pathology is Hepatocellular carcinoma resulting from NASH.

In one embodiment, said intrahepatic cholestatic liver disease is primary sclerosing cholangitis (PSC) or primary biliary cirrhosis (PBC).

In one embodiment, said hepatic pathology is cholangiocarcinoma resulting from PSC.

In another aspect, the invention relates to an isolated anti CCL24 antibody, or any antigen-binding fragment thereof, for use in:

a. reducing elevated serum levels of liver enzymes upon liver damage;
b. reducing liver damage or necrosis; and/or
c. attenuating the transition of hepatic stellate cells (HSC) to myofibroblasts.

In one embodiment, the isolated anti CCL24 antibody may be a monoclonal antibody.

In some embodiments, the isolated anti CCL24 antibody may be a chimeric antibody, a human antibody, a humanized antibody or a fully humanized antibody.

In further embodiments, the antigen-binding fragment thereof is selected from the group consisting of Fv, single chain Fv (scFv), heavy chain variable region capable of binding the antigen, light chain variable region capable of binding the antigen, Fab, F(ab)2' and any combination thereof.

In one embodiment, said antibody is a fully humanized antibody comprising a heavy chain variable region comprising:

a) the complementary determining region VH CDR1 comprising the amino acid sequence denoted by SEQ ID NO. 1 or a variant thereof;
b) the complementary determining region VH CDR2 comprising the amino acid sequence denoted by SEQ ID NO. 2 or a variant thereof; and
c) the complementary determining region VH CDR3 comprising the amino acid sequence denoted by SEQ ID NO. 3 or a variant thereof; and a light chain variable region comprising
d) the complementary determining region VK CDR1 comprising the amino acid sequence denoted by SEQ ID NO. 4 or a variant thereof;
e) the complementary determining region VK CDR2 comprising the amino acid sequence denoted by SEQ ID NO. 5 or a variant thereof; and
f) the complementary determining region VK CDR3 comprising the amino acid sequence denoted by SEQ ID NO. 6 or a variant thereof.

In one embodiment, said antibody is a fully humanized antibody comprising the heavy chain variable region denoted by SEQ ID NO:7 or a variant thereof and the light chain variable region denoted by SEQ ID NO: 8 or a variant thereof.

In one embodiment, said antibody is a fully humanized antibody comprising six CDR sequences as denoted by SEQ ID Nos 1-6, and a heavy chain variable region having at least 90% sequence homology to SEQ ID NO:7 and a light chain variable region having at least 90% sequence homology to SEQ ID NO: 8.

In one embodiment, said antibody binds the same epitope as an antibody comprising:

(a) a heavy chain CDR1 comprising NSGMN (SEQ ID NO: 1), a heavy chain CDR2 comprising WINTYNGEP-TYTDDFKG (SEQ ID NO: 2), and a heavy chain CDR3 comprising HSYGSSYAMDN (SEQ ID NO: 3); and (b) a light chain CDR1 comprising KASQSVDYDGDSYMN (SEQ ID NO: 4), a light chain CDR2 comprising VASNLKS (SEQ ID NO: 5), and a light chain CDR3 comprising QQSNEEPWT (SEQ ID NO: 6). In one embodiment, said antibody is administered in combination with at least one additional therapeutic agent.

In one embodiment, said at least one additional therapeutic agent is selected from the group consisting of farnesoid X receptor (FXR) agonists, peroxisome proliferator-activated receptor (PPAR) agonists, anti-chemokine or anti-cytokine monoclonal antibodies, small molecules, anti-inflammatory agents, anti-fibrotic agents, and steroids.

In another aspect, the present invention provides a pharmaceutical composition comprising a fully humanized antibody comprising a heavy chain variable region comprising:
a) the complementary determining region VH CDR1 comprising the amino acid sequence denoted by SEQ ID NO. 1 or a variant thereof;
b) the complementary determining region VH CDR2 comprising the amino acid sequence denoted by SEQ ID NO. 2 or a variant thereof; and
c) the complementary determining region VH CDR3 comprising the amino acid sequence denoted by SEQ ID NO. 3 or a variant thereof; and a light chain variable region comprising
d) the complementary determining region VK CDR1 comprising the amino acid sequence denoted by SEQ ID NO. 4 or a variant thereof;
e) the complementary determining region VK CDR2 comprising the amino acid sequence denoted by SEQ ID NO. 5 or a variant thereof; and
f) the complementary determining region VK CDR3 comprising the amino acid sequence denoted by SEQ ID NO. 6 or a variant thereof;
and a pharmaceutically acceptable carrier; wherein said pharmaceutical composition is for use in the treatment of hepatic pathologies.

In one embodiment, said fully humanized antibody further comprises a heavy chain variable region having at least 90% sequence homology to SEQ ID NO:7 and a light chain variable region having at least 90% sequence homology to SEQ ID NO: 8. In one embodiment, said pharmaceutical composition is administered in combination with at least one additional therapeutic agent.

In one embodiment, said pharmaceutical composition is administered prior to, concomitantly or subsequently to the administration of said at least one additional therapeutic agent.

In one embodiment, said pharmaceutical composition further comprises at least one additional therapeutic agent.

In one embodiment, said at least one additional therapeutic agent is selected from the group consisting of farnesoid X receptor (FXR) agonists, peroxisome proliferator-activated receptor (PPAR) agonists, anti-chemokine or anti-cytokine monoclonal antibodies, small molecules, anti-inflammatory agents, anti-fibrotic agents, and steroids.

In another aspect, the present invention provides a method of treating hepatic pathologies comprising administering to a patient in need thereof a therapeutically acceptable amount of a fully humanized antibody comprising a heavy chain variable region comprising:

a) the complementary determining region VH CDR1 comprising the amino acid sequence denoted by SEQ ID NO. 1 or a variant thereof;
b) the complementary determining region VH CDR2 comprising the amino acid sequence denoted by SEQ ID NO. 2 or a variant thereof; and
c) the complementary determining region VH CDR3 comprising the amino acid sequence denoted by SEQ ID NO. 3 or a variant thereof; and a light chain variable region comprising
d) the complementary determining region VK CDR1 comprising the amino acid sequence denoted by SEQ ID NO. 4 or a variant thereof;
e) the complementary determining region VK CDR2 comprising the amino acid sequence denoted by SEQ ID NO. 5 or a variant thereof; and
f) the complementary determining region VK CDR3 comprising the amino acid sequence denoted by SEQ ID NO. 6 or a variant thereof, or the pharmaceutical composition of the invention.

In a further aspect, the invention provides a method of reducing serum levels of liver enzymes upon liver damage and/or reducing liver damage or necrosis, and/or attenuating the transition of hepatic stellate cells (HSC) to myofibroblasts, comprising administering to a patient in need thereof a therapeutically acceptable amount of a fully humanized antibody comprising a heavy chain variable region comprising:
a) the complementary determining region VH CDR1 comprising the amino acid sequence denoted by SEQ ID NO. 1 or a variant thereof;
b) the complementary determining region VH CDR2 comprising the amino acid sequence denoted by SEQ ID NO. 2 or a variant thereof; and
c) the complementary determining region VH CDR3 comprising the amino acid sequence denoted by SEQ ID NO. 3 or a variant thereof; and a light chain variable region comprising
d) the complementary determining region VK CDR1 comprising the amino acid sequence denoted by SEQ ID NO. 4 or a variant thereof;
e) the complementary determining region VK CDR2 comprising the amino acid sequence denoted by SEQ ID NO. 5 or a variant thereof; and
f) the complementary determining region VK CDR3 comprising the amino acid sequence denoted by SEQ ID NO. 6 or a variant thereof, or the pharmaceutical composition of the invention.

In some embodiments, said fully humanized antibody comprises a heavy chain variable region having at least 90% sequence homology to SEQ ID NO:7 and a light chain variable region having at least 90% sequence homology to SEQ ID NO: 8.

In one embodiment, the method further comprises administration of at least one additional therapeutic agent.

In one embodiment, said at least one additional therapeutic agent is selected from the group consisting of farnesoid X receptor (FXR) agonists, peroxisome proliferator-activated receptor (PPAR) agonists, anti-chemokine or anti-cytokine monoclonal antibodies, small molecules, anti-inflammatory agents, anti-fibrotic agents, and steroids.

In another aspect, the present invention provides a method of reducing or inhibiting CCR5 activation in a cell comprising administering a fully humanized antibody comprising a heavy chain variable region comprising:

a) the complementary determining region VH CDR1 comprising the amino acid sequence denoted by SEQ ID NO. 1 or a variant thereof;
b) the complementary determining region VH CDR2 comprising the amino acid sequence denoted by SEQ ID NO. 2 or a variant thereof; and
c) the complementary determining region VH CDR3 comprising the amino acid sequence denoted by SEQ ID NO. 3 or a variant thereof; and a light chain variable region comprising
d) the complementary determining region VK CDR1 comprising the amino acid sequence denoted by SEQ ID NO. 4 or a variant thereof;
e) the complementary determining region VK CDR2 comprising the amino acid sequence denoted by SEQ ID NO. 5 or a variant thereof; and
f) the complementary determining region VK CDR3 comprising the amino acid sequence denoted by SEQ ID NO. 6 or a variant thereof.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1B-1D each represents CCR3 staining as measured by PE labeled anti CCR3 antibodies in three NAFLD patients. FIG. 1E-1G each represents corresponding CCR3 staining/side scatter for each of the three NAFLD patients, i.e. levels of CCR3 expression in different blood cells populations. FIG. 1H-1J each represents CCR3 staining using anti CCR3 antibodies in 3 healthy volunteers. FIG. 1K-1M each represents corresponding CCR3 staining/side scatter area for each of the three healthy patients.

FIG. 2A-2C represent liver biopsies of three different patients (Patient A-C, respectively). FIG. 2D shows a biopsy of a healthy liver and serves as a negative control. FIG. 2E shows a biopsy of a lymph node of a healthy subject and serves as a positive control. FIGS. 2F and 2G represent liver sections stained for the chemokine receptor CCR3 in NASH liver biopsies.

FIG. 3D is a graph showing the collagen concentration in wild type mice in comparison with CCL24 knock out mice as measured by sircol. FIG. 3E is a graph showing the NAFLD activating score in MCD (Methionine choline deficient)-induced NASH model in wild type mice in comparison with CCL24 knock out mice. FIG. 3F is a picture of liver histological section of wild type mouse that received a normal diet, HE staining at magnitude ×5 (FIG. 3F) and magnitude ×20 (FIG. 3G). FIG. 3H is a picture of liver histological section of wild type mouse that received a MCD diet, HE staining at magnitude ×5 (FIG. 3H) and magnitude ×20 (FIG. 3I). FIG. 3J is a picture of liver histological section of CCL24 knock out mouse that received a MCD diet, HE staining at magnitude ×5 (FIG. 3J) and magnitude ×20 (FIG. 3K).

FIGS. 4E and 4F are pictures of a liver histological section of a MCD-induced NASH experimental mouse. FIGS. 4G and 4H are pictures of a liver histological section of a MCD-induced NASH experimental mouse treated with 0.05 mg/kg CM101 mouse. FIGS. 4I and 4J are pictures of a liver histological section of a MCD induced NASH experimental mouse treated with 0.5 mg/kg CM101. FIGS. 4K and 4L are pictures of a liver histological section of a MCD induced NASH experimental mouse treated with 5 mg/kg CM101. FIG. 4M is a graph showing NAFLD activity score in MCD induced NASH experimental mouse treated with different concentrations of CM101. FIG. 4N is a graph showing levels of CCL24 in the livers of MCD induced NASH experimental mice treated with different concentrations of CM101. **pv≤0.05.

FIG. 5A-5N are graphs and images showing the effect of treatment with anti-CCL24 monoclonal antibody (CM101—7.5 mg/kg, n=8) or control IgG (n=8) in the STAM model of non-alcoholic steatohepatitis.

FIG. 5A-5D are representative images of H&E-stained liver sections treated with Control IgG (FIG. 5A and FIG. 5B) or with the CM101 antibody (FIG. 5C and FIG. 5D). FIG. 5E is a graph showing NAFLD activity score (NAS). FIG. 5F is a graph showing hepatocyte ballooning score. FIG. 5G and FIG. 5H are images of liver fibrosis assessed by Sirius red staining following treatment with a control IgG. FIG. 5I and FIG. 5J are images of liver fibrosis assessed by Sirius red staining following treatment with the CM101 antibody. FIG. 5K is a graph illustrating the mean Sirius red staining in treated mice with CM101 antibody vs control. FIG. 5L-5M are representative images of liver fibrosis assessed by α-SMA expression in liver sections following treatment with a control IgG (FIG. 5L) or with the CM101 antibody (FIG. 5M). FIG. 5N is a graph comparing α-SMA expression in treated mice with CM101 antibody vs control.

FIG. 6A-6W are graphs and images showing the effect of treatment with anti-CCL24 monoclonal antibody (CM101) in the thioacetamide (TAA) toxicity induced liver fibrosis rat model [Naïve (n=5), TAA induction (n=10) and TAA+ CM101 (2.5 mg/kg) treated rats (n=10)]. FIG. 6A-6I are representative macroscopic images of rat livers including control livers from 3 healthy rats (FIG. 6A-6C), livers from 3 rats with TAA induced fibrosis (FIGS. 6D-6F) and livers from 3 rats with TAA induced fibrosis treated with the CM101 antibody (FIG. 6G-6I). FIG. 6J is a graph presenting the levels of liver enzymes ALP, AST and ALT. FIG. 6K-6T are representative images of H&E-staining and sirius red staining for collagen deposits in liver sections of a naïve animal (FIG. 6K-6L), of two animals with TAA induced fibrosis (FIGS. 6O-6R) and of two animals with TAA induced fibrosis treated with the CM101 antibody (FIG. 6S-6T). FIG. 6U-6V are two graphs illustrating the level of fibrosis (FIG. 6U) and inflammation (FIG. 6V). FIG. 6W is a graph representing the collagen content measured by sircol.

FIG. 7A-7D are FACS figures showing representative CCR3 expression on human PBMCs from healthy control (FIG. 7A-7B) compared to PSC patients (FIG. 7C-7D). FIG. 7E is a graph summarizing the percentage of CCR3 expression in healthy volunteers vs PSC patients. FIG. 7F-7G are pictures showing liver sections from PSC patients stained with anti CCL24 antibody. FIG. 7H-7I are pictures showing liver sections from PSC patients stained with anti CCR3 antibody.

FIG. 8 are graphs presenting liver enzymes (FIGS. 8A-8D), and histological liver assessment including representative pictures (FIGS. 8E-8N) in PSC induced experimental mice model treated with anti-CCL24 monoclonal antibody (CM101 in 5 mg/kg) compared to vehicle. FIG. 8A-8D are graphs presenting ALK phosphatase levels (FIG. 8A), total bilirubin phosphatase levels (FIG. 8B), AST levels (FIG. 8C) and ALT levels (FIG. 8D) in PSC induced experimental mice model treated with the CM101 antibody. FIG. 8E-8N are HE staining of histological liver sections including representative pictures of healthy controls at magnitude ×10 (FIG. 8E) and ×40 (FIG. 8F); ANIT treated mice at magnitude ×10 (FIG. 8I) and ×40 (FIG. 8J) and ANIT treated mice with the CM101 antibody at magnitude ×10 (FIGS. 8K-8M) and ×40 (FIG. 8L-8N).

FIG. 9A-9F are representative images of Sirius red staining for fibrosis in a cholangitis rat model (BDL) in sham operated controls (FIG. 9A and FIG. 9B) (n=5), in animals treated with PBS (FIG. 9C and FIG. 9D) (n=10), and in animals treated with anti-CCL24 monoclonal antibody (CM101) (FIG. 9E and FIG. 9F) (n=10). FIG. 9G is a quantification graph of Sirius red staining for fibrosis in a cholangitis rat model (BDL) treated with anti-CCL24 monoclonal antibody (CM101), PBS or sham operated controls (n=10, 10 and 5 respectively).

FIG. 10A-10E are representative FACS graphs demonstrating the effect of the fully humanized antibody HCM101 on intracellular expression of α-SMA, in non-activated cells (FIG. 10A), in cells activated with high CCL24 levels (NAFDL patient sera) without treatment with the HCM101 antibody (FIG. 10B) or following treatment with the HCM101 antibody (FIG. 10C) and in cells activated with low CCL24 levels (NAFDL patient sera) without treatment with the HCM101 antibody (FIG. 10D) or following treatment with the HCM101 antibody (FIG. 10E).

FIG. 12A is a graph representing recruitment curve of β-arrestin, indicating activation of the CCR3 receptors by binding increasing concentrations of CCL24. RLU—relative light unit.

FIG. 12B is a graph illustrating inhibition of CCL24-dependent CCR3 receptor activation by HCM101. The assay was performed at a constant CCL24 concentration of 80 nM and increasing concentrations of HCM101.

FIG. 12C is a graph illustrating DiscoverX cAMP bioassay for GPCR activation with a curve representing activation of the CCR5 chemokine receptor by increasing concentrations of CCL24.

FIG. 12D is a graph showing the inhibitory effect of different concentrations of HCM101 on activation of CCR5 by CCL24.

FIG. 12E is a graph showing activation of CCR5 (shown as % activity) by incubation with increasing concentrations of human CCL11 (nM).

FIG. 12F is a graph showing the inhibitory effect of different concentrations of HCM101 on activation of CCR5 by CCL11.

DETAILED DESCRIPTION OF EMBODIMENTS

Figure 1A:
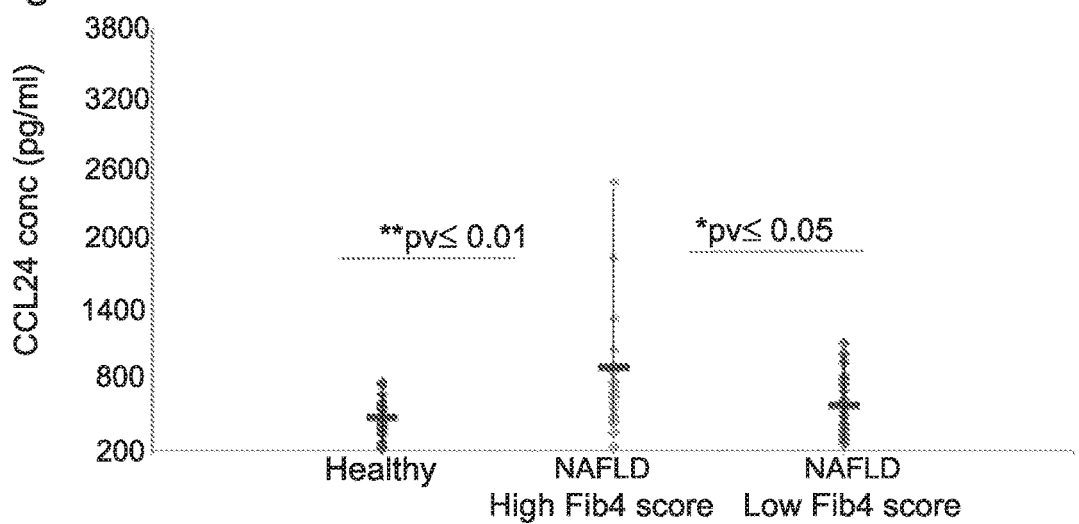
FIG. 1A is a graph showing the circulating systemic levels of CCL24 (eotaxin2) in 55 NAFLD patients divided into low and high Fib4 score, compared with control (20 healthy subjects), as measured by enzyme linked immunosorbent assay (ELISA). The results are presented in picograms per milliliter (pv-P value). Fibrosis 4 score (Fib4) calculation: (Age×AST)/(Platelets×(sqr(ALT)).

The present invention is based on the surprising finding that a monoclonal antibody that is directed to a conformational epitope in the CCL24 (eotaxin2) polypeptide and which binds and inhibits the activity of CCL24 (as well as additional chemotactic agents, the proinflammatory CCR3 binding chemokines: Eotaxin 1, Rantes and MCP-3/1), is useful in the treatment of hepatic pathologies, as demonstrated in animal models of NASH and cholestasis. The anti CCL24 antibody of the invention was effective in reducing serum levels of various liver enzymes (e.g. ALT, AST, alkaline phosphatase and bilirubin) which increase upon liver damage. The antibody of the invention was also effective in reducing liver damage or necrosis in various disease models, as assessed by histological examination, and also attenuated the transition of hepatic stellate cells (HSC) to myofibroblasts. The exemplified anti CCL24 murine monoclonal antibody (termed herein CM101, U.S. Pat. No. 9,067,989) and its humanized version HCM101 (WO 2015/132790) were implicated for use in the treatment of fibrotic diseases, autoimmune inflammatory disorders, monocyte related disorders or allergic atopic disorders. U.S. Pat. No. 9,067,989 and WO 2015/132790 are both incorporated herein by reference.

The present invention provides for the first time a novel use for the antibodies in the treatment of hepatic disorders.

Therefore, in a first of its aspects the present invention provides an isolated anti CCL24 antibody, or any antigen-binding fragment thereof, for use in the treatment of hepatic pathologies.

The terms "eotaxin2" (eosinophil chemotactic protein 2), "CCL24" (Chemokine (C-C motif) ligand 24) or "MPIF-2" (myeloid progenitor inhibitory factor 2) are used interchangeably and refer to a cytokine belonging to the CC chemokine family which is encoded by the human CCL24 gene, located on human chromosome 7. CCL24 interacts with chemokine receptor CCR3. CCL24 activity includes induction of chemotaxis in eosinophils, basophils, T lymphocytes and neutrophils, as well as induction of angiogenic and migratory responses in endothelial and smooth muscle cells.

The term "antibody" refers to a polypeptide encoded by an immunoglobulin gene that specifically binds and recognizes an antigen, namely CCL24.

The anti CCL24 antibody of the invention was previously shown to recognize several, different, proinflammatory CCR3-binding chemokines (WO 2015/132790). The antibody that was generated against CCL24 and was found subsequently to bind and effectively attenuate the activity of additional chemokines (for example, eotaxin 1, Rantes and MCP-3). In one specific embodiment the antibody binds with a higher affinity to CCL24 than to the other tested chemokines. Apparently, the antibody of the invention recognizes a cross-reactive epitope in these proinflammatory CCR3-binding chemokines.

In a preferred embodiment the antibody of the invention is a monoclonal antibody. The term "monoclonal antibody", "monoclonal antibodies" or "mAb" as herein defined refers to a population of substantially homogenous antibodies, i.e., the individual antibodies comprising the population are identical except for possibly naturally occurring mutations that may be present in minor amounts. Monoclonal antibodies are directed against a single antigenic site.

Monoclonal antibodies may be prepared and purified by any method known in the art. For example, monoclonal antibodies may be prepared from B cells taken from the spleen or lymph nodes of immunized animals (e.g. rats or mice), by fusion with immortalized B cells under conditions which favor the growth of hybrid cells.

Immunization of mice may be carried out for example as described in WO 2010/086854. Briefly, immunization of mice may be carried out for example by primary subcutaneous (s.c.) immunization with the desired antigen, namely with CCL24, or with a fragment of the CCL24, preferably comprising a conformational epitope in the N-loop (e.g. 50 µg) emulsified with complete Freund's adjuvant. Two subcutaneous booster injections with the antigen (e.g. 50 µg) emulsified with incomplete Freund's adjuvant are then administered every 2 weeks. The mice with the highest neutralizing antibody titer receive an additional intravenous (i.v.) boost of the antigen (e.g. 5 µg) in PBS four days prior to spleen removal.

After the final boost (e.g. four days), the spleen of the mouse with the highest neutralizing antibody titer is removed and splenocytes are fused to mouse myeloma cells (e.g. NS0 cells) using polyethylene glycol, as previously described (Köhler, G. and Milstein, C. (1975) Nature 256: 495-497). After fusion, the hybridoma cells are selected by growing the cells in HAT (hypoxanthine-aminopterin-thymidine) medium. Cell clones are then screened for specific antibody production, for example using the ELISA assays described below.

Purification of monoclonal antibodies may be based for example on affinity chromatography, namely, using an affinity column to which the specific epitope is conjugated.

An exemplary antibody structural unit comprises a tetramer, as known in the art. Each tetramer is composed of two identical pairs of polypeptide chains, each pair having one "light chain" and one "heavy chain". The N-terminus of each chain defines a variable region of about 100 to 110 or more amino acids primarily responsible for antigen (or epitope) recognition.

Thus, the terms "heavy chain variable region" ($V_H$) and "light chain variable region" ($V_L$) refer to these heavy and light chains, respectively. More specifically, the variable region is subdivided into hypervariable and framework (FR) regions. Hypervariable regions have a high ratio of different amino acids in a given position, relative to the most common amino acid in that position. Four FR regions which have more stable amino acids sequences separate the hypervariable regions. The hypervariable regions directly contact a portion of the antigen's surface. For this reason, hypervariable regions are herein referred to as "complementarity determining regions", or "CDRs".

From N-terminal to C-terminal, both light and heavy chains comprise the domains FR1, CDR1, FR2, CDR2, FR3, CDR3 and FR4. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located.

Thus, the complementarity determining regions CDRH1, CDRH2 and CDRH3 refer to the three complementarity determining regions starting from the N-terminus of the antibody's heavy chain and the complementarity determining regions CDRL1, CDRL2 and CDRL3 refer to the three complementarity determining regions starting from the N-terminus of the antibody's light chain.

In some embodiments the isolated anti CCL24 monoclonal antibody is a chimeric antibody, a human antibody, a humanized antibody or a fully humanized antibody.

The term "chimeric" antibodies as herein defined refers to antibodies in which a portion of the heavy and/or light chain is derived from a particular species, while the remainder of the chain(s) is derived from another species.

Chimeric antibodies may be prepared by any method known in the art, for example as described below.

A murine-human chimeric antibody may be prepared by the amplification and cloning of murine $V_H$ and $V_L$ genes, encoding the antibody variable regions, followed by murine-human chimeric antibody expression. To this end, total RNA is isolated from murine anti-CCL24 hybridoma cells that are shown to secrete antibodies with the desired characteristics and cDNA is synthesized using oligo $(dT)_{15}$ primer, M-MLV and AMV reverse transcriptases. Amplification of the heavy and the light variable genes ($V_H$ and $V_L$) may be carried out using a panel of primers directed at the 5' terminus of framework 1 of each gene, essentially as described in Benhar and Reiter (Benhar, I. and Reiter, Y. (2002) Curr. Protoc. Immunol. Chapter 10: Unit 10 19B), and to the constant region ($C_H1$ or $C_k$, respectively) at the 3' end.

The variable genes are then re-amplified using non-degenerate primers introducing restriction sites at both ends for cloning, for example, into a pCMV-based antibody expression vector.

The amplified heavy and light variable genes are separately purified, digested and cloned into appropriate mammalian full-length Ig expression vectors, providing each chain with a corresponding signal-peptide and constant gene, resulting in IgG1/k murine human chimeric antibody expression.

The term "humanized" antibodies traditionally refers to forms of non-human (for example, murine) antibodies that contain a human-derived immunoglobulin framework with minimal sequences derived from non-human immunoglobulin at the CDRs and optionally at additional relevant positions. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and activity.

As used herein the term "fully humanized" antibodies relates to antibodies designed to have only human sequences. The fully humanized antibodies of the present invention were prepared using the Composite Human Antibodies™ technology that minimizes immunogenicity of the antibodies in patients. In this humanization technology multiple sequence segments derived from variable (V) regions of unrelated human antibodies are used as acceptors for the complementarity determining regions (CDRs) of the starting antibodies. Through careful selection of human sequence segments and the application of in silico tools, CD4+ T cell epitopes are avoided so the risk of immunogenicity is reduced compared to standard humanized antibodies whilst antibody affinity and specificity is maintained. Such antibodies contain only human sequences and are thus defined as "fully humanized".

The term "human antibody" as used herein refers to an antibody that possesses an amino acid sequence corresponding to that of an antibody produced by a human and/or has been made using any of the techniques for making human antibodies known in the art. This definition specifically excludes a humanized antibody that comprises non-human antigen-binding residues.

Preparation of humanized and human antibodies is well known in the art. Antibodies may also be prepared using phage display. As known in the art, antibody phage display (APD) is based on genetic engineering of bacteriophages and repeated rounds of antigen-guided selection and phage propagation.

The APD process begins with antibody-library preparation, by preparation of quality RNA from the cell source chosen (e.g., peripheral blood mononuclear cells). This RNA is reverse-transcribed into cDNA, which is used for PCR of the VH and VL chains of the encoded antibodies. This step is followed by ligation of the variable heavy (VH) and variable light (VL) PCR products into a phage display vector, culminating in analysis of clones of mAbs.

For preparing large quantities of the antibody (either chimeric, humanized, fully humanized or human), a stable cell line expressing the antibody can be prepared, by transfecting cells (e.g. CHO cells) with the Ig expression vector containing both heavy and light chains of the antibody. The antibodies may then be manufactured in a state of the art single-use bioreactor system. The antibodies may be purified to clinical grade using well established monoclonal antibody purification methods. Highly anti-CCL24 antibody producing clones may be then selected and expanded based on antibody levels in the supernatant, as tested by any method known in the art, for example, an CCL24-specific ELISA assay, as detailed herein below. A master cell bank, developed for the specific clone, may serve as the starting growing material for all clinical grade batches.

In some embodiments the present invention provides an isolated anti CCL24 murine antibody (termed herein CM101), or any antigen-binding fragment thereof, for use in the treatment of hepatic diseases, wherein said antibody is selected from the group consisting of:
  a. a monoclonal antibody comprising a heavy chain encoded by a nucleic acid having at least 90% homology with SEQ ID NO: 9 and a light chain encoded by a nucleic acid having at least 90% homology with SEQ ID NO: 10, or a fragment thereof which retains the binding activity of the antibody; and
  b. a monoclonal antibody secreted by hybridoma D8 (ECACC Accession No. D 809081702), or a fragment thereof which retains the binding activity of the antibody.

```
The nucleic acid sequence
encoding for the murine antibody
CM101 heavy chain is denoted as SEQ ID NO: 9:
GGGCAGCAGANCCGGGGCNGNGGATAGACAGANGGGGGNNGNCGTTTTGG

CTGAGGAGACGGTGACTGAGGTTCCTTGACCCCAGTTGTCCATAGCGTAG

CTACTACCGTAGGAATGACTTGCACAGAAATATGTAGCCGTGTCCTCATT

TCTGAGGTTGTTGATCTGCAAATAGGCAGTGCTGGCAGAGGTTTCCAAAG
```

```
-continued
AGAGGGCAAACCGTCCCTTGAAGTCATCAGTATATGTTGGCTCTCCATTG

TAGGTGTTGATCCAGCCCATCCACTTTAAACCCTTTCCTGGAGCCTGCTT

TACCCAGTTCATTCCAGAGTTTGTGAAGGGATACCCAGAAGCCCTGCAGG

AGATCTTGACTGTGTCTCCAGGCTTCTTCAGCTCANGTCCAGACTGCACC

AACTGGATCTGGGCCATGGCCNGCTA

The nucleic acid sequence encoding
for the murine antibody CM101 light
chain (kappa) is denoted as SEQ ID NO: 10:
GGGCCAATGGNNGAGGACGCGGATGGGGGTGTCGNNGTGCCTTNGTCGNN

NNCTNNTTGNNCANCNTCNACNNCNNNNANNNNANNGNNNNNTGNAANAN

NGATGGNNNTNNNCNACANNNTGGNNTCCTNNNNNNNTNNNNTGNNNNNG

ACNNCANANACANNNNCNACNNNATGANCNNCNNNCNNNNNTTGANNNNN

GNCNANTATGAACNANNNAANNNNNNTACCTGNNANGCCACTCACAAGAC

ATCA
```

The invention also encompasses humanized and fully humanized versions of the antibody CM101.

In some embodiments the present invention provides a fully humanized isolated anti CCL24 antibody (termed herein HCM101), or any antigen-binding fragment thereof, for use in the treatment of hepatic diseases, wherein said antibody comprises a heavy chain variable region comprising:
  a) the complementary determining region VH CDR1 comprising the amino acid sequence denoted by SEQ ID NO. 1 or a variant thereof;
  b) the complementary determining region VH CDR2 comprising the amino acid sequence denoted by SEQ ID NO. 2 or a variant thereof; and
  c) the complementary determining region VH CDR3 comprising the amino acid sequence denoted by SEQ ID NO. 3 or a variant thereof; and a light chain variable region comprising
  d) the complementary determining region VK CDR1 comprising the amino acid sequence denoted by SEQ ID NO. 4 or a variant thereof;
  e) the complementary determining region VK CDR2 comprising the amino acid sequence denoted by SEQ ID NO. 5 or a variant thereof; and
  f) the complementary determining region VK CDR3 comprising the amino acid sequence denoted by SEQ ID NO. 6 or a variant thereof.

In accordance with the invention VH CDR1 comprises the amino acid sequence NSGMN denoted by SEQ ID NO. 1, or a variant thereof; VH CDR2 comprises the amino acid sequence WINTYNGEPTYTDDFKG denoted by SEQ ID NO. 2, or a variant thereof, VH CDR3 comprises the amino acid sequence HSYGSSYAMDN denoted by SEQ ID NO. 3 or a variant thereof; VK CDR1 comprises the amino acid sequence KASQSVDYDGDSYMN denoted by SEQ ID NO. 4 or a variant thereof; VK CDR2 comprises the amino acid sequence VASNLKS denoted by SEQ ID NO. 5 or a variant thereof; and VK CDR3 comprises the amino acid sequence QQSNEEPWT denoted by SEQ ID NO. 6 or a variant thereof.

In one specific embodiment, the present invention provides an isolated anti CCL24 antibody, or any antigen-binding fragment thereof, comprising the complementary determining region VH CDR3 comprising the amino acid sequence HSYGSSYAMDN denoted by SEQ ID NO. 3, for use in the treatment of hepatic pathologies.

The above CDR sequences CDRH1, CDRH2, CDRH3, CDRL1, CDRL2 and CDRL3 denoted by SEQ ID NO. 1, SEQ ID NO. 2, SEQ ID NO. 3, SEQ ID NO. 4, SEQ ID NO. 5 and SEQ ID NO. 6, respectively are also presented in the context of their respective heavy and light chains sequences:

The amino acid sequence of the heavy chain of the isolated fully humanized polyspecific monoclonal antibody exemplified herein is denoted by SEQ ID NO: 7 and is of the amino acid sequence:

QIQLVQSGPELKKPGASVKVSCRASGYPFTNSGMNWVKQAPGKGLKWMGW

INTYNGEPTYTDDFKGRFAFSLETSASTAYLQINNLRNEDTATYFCASHS

YGSSYAMDNWGQGTSVTVSS

The amino acid sequence of the light chain of the isolated humanized polyspecific monoclonal antibody exemplified herein is denoted herein by SEQ ID NO: 8 and is of the amino acid sequence:

DIVLTQSPDSLAVSLGERATINCKASQSVDYDGDSYMNWYQQKPGQPPKL

LIYVASNLKSGIPARFSGSGSGTDFTLTISSLQPEDFATYYCQQSNEEPW

TFGGGTKVEIK

Therefore in further embodiments the isolated antibody for use according to the invention is wherein said antibody is a fully humanized antibody comprising the heavy chain variable region denoted by SEQ ID NO:7 or a variant thereof and the light chain variable region denoted by SEQ ID NO: 8 or a variant thereof.

In another embodiment the isolated antibody for use according to the invention is wherein said antibody is a fully humanized antibody comprising six CDR sequences as denoted by SEQ ID Nos 1-6, and a heavy chain variable region having at least 90% sequence homology to SEQ ID NO:7 and a light chain variable region having at least 90% sequence homology to SEQ ID NO: 8.

In another embodiment, the present invention provides an isolated monoclonal antibody that binds the same epitope as an antibody comprising:

(a) a heavy chain CDR1 comprising NSGMN (SEQ ID NO: 1), a heavy chain CDR2 comprising WINTYNGEP-TYTDDFKG (SEQ ID NO: 2), and a heavy chain CDR3 comprising HSYGSSYAMDN (SEQ ID NO: 3); and (b) a light chain CDR1 comprising KASQSVDYDGDSYMN (SEQ ID NO: 4), a light chain CDR2 comprising VASNLKS (SEQ ID NO: 5), and a light chain CDR3 comprising QQSNEEPWT (SEQ ID NO: 6), for use in the treatment of hepatic pathologies.

The present invention also provides methods of treating hepatic pathologies comprising administering to a subject in need thereof the antibody as defined above.

In another embodiment, the isolated antibody for use according to the invention is wherein said antibody is a fully humanized antibody comprising a heavy chain variable region encoded by a nucleic acid sequence denoted by SEQ ID NO:11 or a variant thereof and a light chain variable region encoded by a nucleic acid sequence denoted by SEQ ID NO: 12 or a variant thereof.

SEQ ID NO: 11:
CAGATCCAATTGGTGCAGTCTGGACCTGAGCTGAAGAAGCCTGGAGCCTC

AGTCAAGGTCTCCTGCAGGGCTTCTGGGTATCCCTTCACAACTCTGGAA

TGAACTGGGTAAAGCAGGCTCCAGGAAAGGGTTTAAAGTGGATGGGCTGG

ATCAACACCTACAATGGAGAGCCAACATATACTGATGACTTCAAGGGACG

GTTTGCCTTCTCTTTGGAAACCTCTGCCAGCACTGCCTATTTGCAGATCA

ACAACCTCAGAAATGAGGACACGGCTACATATTTCTGTGCAAGTCATTCC

TACGGTAGTAGCTACGCTATGGACAACTGGGGTCAAGGAACCTCAGTCAC

CGTCTCCTCA

SEQ ID NO: 12:
GACATTGTGCTGACCCAATCTCCAGACTCTTTGGCTGTGTCTCTAGGGGA

GAGGGCCACCATCAACTGCAAGGCCAGCCAAAGTGTTGATTATGATGGTG

ATAGTTATATGAACTGGTACCAACAGAAACCAGGACAGCCACCCAAACTC

CTCATCTATGTTGCATCCAATCTAAAATCTGGCATCCCAGCCAGGTTTAG

TGGCAGTGGGTCTGGGACAGACTTCACCCTCACCATCAGCAGCCTGCAGC

CTGAGGATTTTGCAACCTATTACTGTCAGCAAAGTAATGAGGAACCGTGG

ACGTTCGGTGGAGGCACCAAGGTGGAAATCAAA
*CDR nucleotide sequences are bolded and underlined.

The present invention also encompasses variants of the heavy and light chain variable regions. The variants may include mutations in the complementarity determining regions of the heavy and light chains which do not alter the activity of the antibodies herein described, or in the framework region.

By the term "variant" it is meant sequences of amino acids or nucleotides different from the sequences specifically identified herein, in which one or more amino acid residues or nucleotides are deleted, substituted or added.

It should be appreciated that by the term "added", as used herein it is meant any addition of amino acid residues to the sequences described herein.

Variants encompass various amino acid substitutions. An amino acid "substitution" is the result of replacing one amino acid with another amino acid which has similar or different structural and/or chemical properties. Amino acid substitutions may be made on the basis of similarity in polarity, charge, solubility, hydrophobicity, hydrophilicity, and/or the amphipathic nature of the residues involved.

Typically, variants encompass conservative amino acid substitutions. Conservative substitution tables providing functionally similar amino acids are well known in the art. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Each of the following eight groups contains other exemplary amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);

6) Phenylalanine (F), Tyrosine (Y), Tryptophan (W);
7) Serine (S), Threonine (T); and
8) Cysteine (C), Methionine (M).

Conservative nucleic acid substitutions are nucleic acid substitutions resulting in conservative amino acid substitutions as defined above.

Variants in accordance with the invention also encompass non-polar to polar amino acid substitutions and vice-versa.

As used herein, the term "amino acid" or "amino acid residue" refers to naturally occurring and synthetic amino acids, as well as amino acid analogs and amino acid mimetics that function in a manner similar to the naturally occurring amino acids.

Variant sequences refer to amino acid or nucleic acids sequences that may be characterized by the percentage of the identity of their amino acid or nucleotide sequences with the amino acid or nucleotide sequences described herein (for example, the amino acid or nucleotide sequences of the heavy and light chains of the antibodies herein described).

In some embodiments, variant sequences as herein defined refer to nucleic acid sequences that encode the heavy and light chain variable regions, each having a sequence of nucleotides with at least 70% or 75% of sequence identity, around 80% or 85% of sequence identity, around 90%, 91%, 92%, 93%, 94%, 95%, 96%, 97%, 98% or 99% of sequence identity when compared to the sequences of the heavy and light chain variable regions described herein.

The terms "hepatic pathology" or "liver disease" are used interchangeably herein and relate to any disorder of the liver. Liver pathologies generally include cirrhosis, or scarring of the liver, inflammation (hepatitis) caused by infectious (e.g. hepatitis B or hepatitis C) or non-infectious causes (chemical or autoimmune hepatitis including alcoholic steatohepatitis), tumors, benign and malignant (liver cancer) and metabolic disorders. In certain embodiments, the invention provides an anti CCL24 antibody for use in the treatment of hepatic pathologies such as non-alcoholic fatty liver disease (NAFLD, including nonalcoholic fatty liver (NAFL) and nonalcoholic steatohepatitis (NASH)), cholestasis and intrahepatic cholestatic liver diseases such as primary sclerosing cholangitis (PSC) and primary biliary cirrhosis (PBC).

The invention also provides an isolated anti CCL24 antibody, or any antigen-binding fragment thereof, for use in:
  a. reducing elevated serum levels of liver enzymes (e.g. ALT, AST, alkaline phosphatase and bilirubin) upon liver damage;
  b. reducing liver damage or necrosis; and/or
  c. attenuation of the transition of hepatic stellate cells (HSC) to myofibroblasts.

In some embodiments said elevated levels of liver enzymes or said liver damage or necrosis are caused by a hepatic liver pathology, as defined above.

In some embodiments said isolated anti CCL24 antibody is a murine antibody (termed herein CM101), or any antigen-binding fragment thereof, wherein said antibody is selected from the group consisting of:
  a. a monoclonal antibody comprising a heavy chain encoded by a nucleic acid having at least 90% homology with SEQ ID NO: 9 and a light chain encoded by a nucleic acid having at least 90% homology with SEQ ID NO: 10, or a fragment thereof which retains the binding activity of the antibody; and
  b. a monoclonal antibody secreted by hybridoma D8 (ECACC Accession No. D 809081702), or a fragment thereof which retains the binding activity of the antibody.

In some embodiments said isolated anti CCL24 antibody is a fully humanized antibody (termed herein HCM101), or any antigen-binding fragment thereof, wherein said antibody comprises a heavy chain variable region comprising:
  a) the complementary determining region VH CDR1 comprising the amino acid sequence denoted by SEQ ID NO. 1 or a variant thereof;
  b) the complementary determining region VH CDR2 comprising the amino acid sequence denoted by SEQ ID NO. 2 or a variant thereof; and
  c) the complementary determining region VH CDR3 comprising the amino acid sequence denoted by SEQ ID NO. 3 or a variant thereof; and a light chain variable region comprising
  d) the complementary determining region VK CDR1 comprising the amino acid sequence denoted by SEQ ID NO. 4 or a variant thereof;
  e) the complementary determining region VK CDR2 comprising the amino acid sequence denoted by SEQ ID NO. 5 or a variant thereof; and
  f) the complementary determining region VK CDR3 comprising the amino acid sequence denoted by SEQ ID NO. 6 or a variant thereof.

By the term "activity of the antibodies" it is meant the ability of the antibodies to bind CCL24, and preferably to inhibit a biological function mediated by CCL24, for example, inhibition of cell recruitment or chemotaxis (e.g. recruitment or chemotaxis of eosinophils or monocytes or fibroblasts). The biological functions can be measured in vivo or in vitro using methods well known in the art. Several such in vivo assays are described in the Examples below.

The binding of the antibody of the invention to its target protein may be measured for example using ELISA assays.

The present invention further encompasses any antigen-binding fragments of the isolated anti CCL24 monoclonal antibody of the invention. Such antigen-binding fragments may be for example Fab and F (ab')$_2$, which are capable of binding antigen. Such fragments may be produced by any method known in the art, for example by proteolytic cleavage, using enzymes such as papain (to produce Fab fragments) or pepsin (to produce F(ab')$_2$ fragments).

Thus in some embodiments an antibody fragment is selected from the group consisting of Fv, single chain Fv (scFv), heavy chain variable region capable of binding the antigen, light chain variable region capable of binding the antigen, Fab, F(ab)$_2$' and any combination thereof.

In another one of its aspects the present invention provides an isolated nucleic acid molecule comprising a nucleotide sequence encoding an antibody or any antigen-binding fragment thereof according to the invention, wherein said antibody is for use in the treatment of hepatic diseases.

The term "nucleic acid" or "nucleic acid molecule" as herein defined refers to a polymer of nucleotides, which may be either single- or double-stranded, which is a polynucleotide such as deoxyribonucleic acid (DNA), and, where appropriate, ribonucleic acid (RNA). The terms should also be understood to include, as equivalents, analogs of either RNA or DNA made from nucleotide analogs, and, as applicable to the embodiment being described, single-stranded (such as sense or antisense) and double-stranded polynucleotides. The term DNA used herein also encompasses cDNA, i.e. complementary or copy DNA produced from an RNA template by the action of reverse transcriptase (RNA-dependent DNA polymerase).

The invention further provides an expression vector comprising the isolated nucleic acid molecule as herein defined.

"Expression vector" sometimes referred to as "expression vehicle" or "expression construct", as used herein, encompasses vectors such as plasmids, viruses, bacteriophage, integratable DNA fragments, and other vehicles, which enable the integration of DNA fragments into the genome of the host. Expression vectors are typically self-replicating DNA or RNA constructs containing the desired gene or its fragments, and operably linked genetic control elements that are recognized in a suitable host cell and effect expression of the desired genes. These control elements are capable of effecting expression within a suitable host. The expression vector in accordance with the invention may be competent with expression in bacterial, yeast, or mammalian host cells, to name but few.

In yet another one of its aspects the present invention provides a host cell transfected with the isolated nucleic acid molecule according to the invention or with the expression vector according to the invention.

The term "host cells" as used herein refers to cells which are susceptible to the introduction of the isolated nucleic acid molecule according to the invention or with the expression vector according to the invention. Preferably, said cells are mammalian cells, for example CHO cells or NS0 cells. Transfection of the isolated nucleic acid molecule or the expression vector according to the invention to the host cell may be performed by any method known in the art.

In yet another one of its aspects the present invention provides an immunoconjugate comprising the antibody or any antigen-binding fragment thereof according to the invention and an additional therapeutic agent as defined herein below.

The term "immunoconjugate" as herein defined refers to an antibody or any antigen-binding fragment thereof according to the invention that is conjugated (linked or joined) to an additional agent. Immunoconjugates may be prepared by any method known to a person skilled in the art, for example, by cross-linking the additional agent to the antibody according to the invention or by recombinant DNA methods.

The anti CCL24 antibody of the invention may be administered in combination with at least one additional therapeutic agent.

The term "additional therapeutic agent" used herein refers to any agent that may be used for treating hepatic diseases. In accordance with certain embodiments said at least one additional therapeutic agent is selected from a group consisting of chemotherapeutics, cytokines, peptides, antibodies and antibiotics.

In certain embodiments, said additional therapeutic agent includes, but is not limited to farnesoid X receptor (FXR) agonists (e.g. cafestol, chenodeoxycholic acid, obeticholic acid, fexaramine), peroxisome proliferator-activated receptor (PPAR) agonists, anti-chemokine or cytokine monoclonal antibodies, small molecules which inhibit chemokine or cytokine functions, anti-inflammatory and anti-fibrotic agents, including steroids and soluble protein anti-inflammatory agents.

In certain embodiments the additional therapeutic agent is an additional antibody. The term "additional antibody" as herein defined refers to an antibody, which is not the antibody according to the invention, which may be used in combination with the antibody of the invention.

The present invention further provides a pharmaceutical composition comprising as an active ingredient the isolated anti CCL24 antibody of the invention, or any antigen-binding fragment thereof or the immunoconjugate as herein defined and a pharmaceutically acceptable carrier, excipient or diluent, wherein said pharmaceutical composition is for use in the treatment of hepatic diseases, and/or for use in:

a. reducing elevated serum levels of liver enzymes (e.g. ALT, AST, alkaline phosphatase and bilirubin) upon liver damage;

b. reducing liver damage or necrosis; and/or c. attenuation of the transition of hepatic stellate cells (HSC) to myofibroblasts.

The "pharmaceutical composition" of the invention generally comprises the antibody or any antigen-binding fragment thereof as herein defined and a buffering agent, an agent which adjusts the osmolarity of the composition and optionally, one or more pharmaceutically acceptable carriers, excipients and/or diluents as known in the art.

As used herein the term "pharmaceutically acceptable carrier, excipient or diluent" includes any and all solvents, dispersion media, coatings, antibacterial and antifungal agents and the like, as known in the art. The carrier can be solvent or dispersion medium containing, for example, water, ethanol, polyol (for example, glycerol, propylene glycol, and liquid polyethylene glycol, and the like), suitable mixtures thereof, and vegetable oils. Each carrier should be both pharmaceutically and physiologically acceptable in the sense of being compatible with the other ingredients and not injurious to the subject. Except as any conventional media or agent is incompatible with the active ingredient, its use in the therapeutic composition is contemplated.

In other embodiments the pharmaceutical composition according to the invention further comprises an additional therapeutic agent. Non-limiting examples of additional therapeutic agents include FXR agonists, PPAR agonists, anti-chemokine or anti-cytokine monoclonal antibodies, or any small molecule, protein or peptide that inhibit the activity of a chemokine or cytokine, anti-inflammatory agents including steroids and anti-fibrotic agents.

In specific embodiments the present invention relates to a pharmaceutical composition comprising an isolated anti CCL24 fully humanized antibody, or any antigen-binding fragment thereof, wherein the antibody comprises a heavy chain variable region of the amino acid sequence denoted by SEQ ID NO. 7 or a variant thereof and a light chain variable region of the amino acid sequence denoted by SEQ ID NO. 8, or a variant thereof, wherein said pharmaceutical composition is for use in the treatment of hepatic diseases.

Further provided is a method of prophylaxis, treatment or amelioration of hepatic diseases, comprising administering to a subject in need thereof a therapeutically effective amount of the isolated anti CCL24 antibody or any antigen-binding fragment thereof or the pharmaceutical composition according to the invention.

Also provided is a method of reducing elevated serum levels of liver enzymes (e.g. ALT, AST, alkaline phosphatase and bilirubin) upon liver damage, comprising administering to a subject in need thereof a therapeutically effective amount of the isolated anti CCL24 antibody or any antigen-binding fragment thereof or the pharmaceutical composition according to the invention.

Also provided is a method of reducing liver damage or necrosis, comprising administering to a subject in need thereof a therapeutically effective amount of the isolated anti CCL24 antibody or any antigen-binding fragment thereof or the pharmaceutical composition according to the invention.

Also provided is a method of attenuating the transition of hepatic stellate cells (HSC) to myofibroblasts, comprising administering to a subject in need thereof a therapeutically effective amount of the isolated anti CCL24 antibody or any antigen-binding fragment thereof or the pharmaceutical composition according to the invention.

The terms "subject" or "patient" are used interchangeably and refer to a subject that may benefit from the present invention such as a mammal (e.g. canine, feline, ovine, porcine, equine, bovine, or human). In one specific embodiment the patient is human.

By the term "prophylaxis" as herein defined it is meant to provide a "preventive treatment" or "prophylactic treatment", namely acting in a protective manner, to defend against or prevent the appearance of a symptom of a hepatic disease, or hepatic disease onset or progression.

It is to be understood that the terms "treat", "treating", "treatment" or forms thereof, as used herein, mean reducing, preventing, curing, reversing, ameliorating, attenuating, alleviating, minimizing, suppressing or halting the deleterious effects of a disease or a condition or delaying the onset of one or more clinical indications of hepatic diseases, as defined herein.

Administration according to the present invention may be performed by any of the following routes: oral administration, intravenous, intramuscular, intraperitoneal, intratechal or subcutaneous injection; intrarectal administration; intranasal administration, ocular administration or topical administration.

In specific embodiments administration according to the present invention may be performed intravenously. In other specific embodiments administration may be performed intraperitoneally. In other specific embodiments administration may be performed by inhalation.

The antibodies or antibody fragments as herein defined, any pharmaceutical compositions comprising the same or any conjugates comprising them may be administered to a subject prior to or post disease onset.

Thus in some embodiments the method of prophylaxis, treatment or amelioration of hepatic diseases according to the invention is where said isolated anti CCL24 antibody or any antigen-binding fragment thereof according to the invention, or pharmaceutical composition according to the invention is administered to said subject prior to or after disease onset.

A "therapeutically effective amount" of the isolated monoclonal antibody or any antigen-binding fragment thereof according to the invention, or the pharmaceutical composition according to the invention for purposes herein defined is determined by such considerations as are known in the art in order to cure, arrest or at least alleviate or ameliorate the medical condition. For any preparation used in the methods of the invention, the dosage or the therapeutically effective amount can be estimated initially from in vitro cell culture assays or based on animal models such as the animal models detailed herein.

In some embodiments the therapeutically effective amount in accordance with the invention is in the range of 0.01 to 100 mg/kg.

In other embodiments the therapeutically effective amount in accordance with the invention is in the range of 0.01 to 40 mg/kg, 0.1 to 40 mg/kg, 1 to 10 mg/kg, or 5 to 10 mg/kg.

In other embodiments the isolated anti CCL24 antibody or any antigen-binding fragment thereof according to the invention or pharmaceutical composition according to the invention is administered to the subject as a single dose or as multiple doses.

Specific exemplary doses include, but are not limited to, 0.75 mg/kg, or 2.5 mg/kg, or 5 mg/kg, or 10 mg/kg each given as a single daily dose. In one embodiment, the doses are given intravenously.

The term "subject in need thereof" in the context of the present invention refers to mammals and in particular to human subjects suffering from a hepatic disease as defined herein.

The present invention further provides the isolated anti CCL24 antibody or any antigen-binding fragment thereof according to the invention or the pharmaceutical composition according to the invention for use in a method of prophylaxis, treatment or amelioration of a hepatic disease as defined herein.

In specific embodiments the invention provides an isolated fully humanized anti CCL24 antibody, or any antigen-binding fragment thereof, wherein the antibody comprises a heavy chain variable region of the amino acid sequence denoted by SEQ ID NO. 7 or a variant thereof and a light chain variable region of the amino acid sequence denoted by SEQ ID NO. 8, or a variant thereof for use in a method of prophylaxis, treatment or amelioration of a hepatic disease as defined herein.

It is appreciated that the term "purified" or "isolated" refers to molecules, such as amino acid or nucleic acid sequences, peptides, polypeptides or antibodies that are removed from their natural environment, isolated or separated. An "isolated antibody" is therefore a purified antibody. As used herein, the term "purified" or "to purify" also refers to the removal of contaminants from a sample.

As shown in the Examples below, the antibody of the invention is able to reduce or inhibit activation of both chemokine receptors CCR3 and CCR5. Moreover, the antibody of the invention was capable of inhibiting both CCL24-induced and CCL11-induced activation of CCR5.

Accordingly, in another aspect, the present invention provides a method of inhibiting CCR5 activation in cells comprising administering the antibody of the invention as defined above.

The antibody of the invention can therefore be employed in the treatment of diseases or disorders associated with CCR5 activation. None limiting examples of such diseases or disorders are hepatic pathologies as defined above.

EXAMPLES

Without further elaboration, it is believed that one skilled in the art can, using the preceding description, utilize the present disclosure to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook & Russell, 2001.

Standard medicinal chemistry methods known in the art not specifically described herein are generally followed essentially in the series "Comprehensive Medicinal Chemistry" by various authors and editors, published by Pergamon Press.

Materials and Methods

Chemokines Levels in the Sera of Human Subjects

Eotaxin-2 levels were determined in the sera of NASH and primary sclerosing cholangitis (PSC) patients and healthy donors using the following ELISA kits: Quantikine human CCL24 (eotaxin2) (R&D), according to the manufacturer's protocol.

Immunohistochemistry of Liver Biopsies of Human Patients

Immunohistochemical staining for human CCL24 was performed on 5-μm-thick frozen sections of liver biopsies from NASH patients. After fixation with methanol and acetone, sections were blocked with nonimmune rabbit and goat sera, followed by incubation with CAS blocking reagent. Subsequently, the primary antibody was added for 1 hour at room temperature. After washing, biotinylated affinity-purified goat anti-mouse/rabbit antibodies (Jackson) were added. The slides were then incubated with 0.3% H2O2, followed by additional rinses and incubation with streptavidin-peroxidase conjugate (Jackson) for 30 minutes at room temperature. The slides were developed with 3-amino-9 ethylcarbazole substrate (Dako) for 15 minutes and counterstained with hematoxylin. Hematoxylin eosin (H&E) stains were used for analysis of NAFLD activating score changes in liver sections.

CCL24 Levels in Liver Samples from Mice

Liver tissue obtained from mice were weighted and suspended in lysis buffer (for each 10 mg of tissue −100 μl lysis buffer containing anti proteases was added). Tissue was then smashed with Polytron and Centrifuged for 10 minutes at 14000 rpm at 4° c. Pellet was discarded and supernatant was assayed for CCL24 levels using a commercial ELISA Kit (Abcam).

H&E Staining in Mice Liver Sections

Livers from mice, two liver lobes per animal, were harvested and fixed in 2.5% paraformaldehyde (PFA) on the sacrifice day. Tissues were trimmed, embedded in paraffin, sectioned at no more than 5 microns thickness, and stained with Hematoxylin & Eosin (H&E). Pictures were taken using microscope (Olympus BX60) at magnifications of ×10, ×20 and ×40.

The following parameters were evaluated for the calculation of NAFLD activity score according to the acceptable score defined by The Pathology Committee of the NASH Clinical Research Network (Kleiner et al 2015 HEPATOLOGY, Vol. 41, No. 6). The score is defined as the unweighted sum of the scores for steatosis (0-3), lobular inflammation (0-3), and ballooning (0-2); thus ranging from 0 to 8:

1. Steatosis (Low- to medium-power evaluation of parenchymal involvement) (0≤5%, 1-5-33%, 2-33-66%, 3≥66%).
2. Inflammation (Overall assessment of all inflammatory foci) (0=no Foci, 1 ≤2 foci per 200× field, 2: 2-4 Foci per 200× field, 3: ≥4 Foci per 200× field.)

Ballooning (0=none, 1=few balloon changes, 2=Many cells/prominent ballooning)

Sirius Red Staining in Rat Liver Sections

Liver tissues were fixed with 10% buffered neutral formalin and embedded in paraffin. Sections (4 μm) were deparaffinized and stained with picro-Sirius red for 15 min at room temperature (RT), dehydrated and mounted with mounting medium. Liver fibrosis was measured in the stained sections using an OsteoMeasure image analysis software program (OsteoMetrics, Inc., Atlanta, Ga.) interfaced with an Olympus light/epifluorescent microscope and video subsystem. For assessment of fibrosis in picro-Sirius red stained sections from STAM mice, collagen deposition was visualized and quantified by bright field images (40 fields each slide) of stained sections using a digital camera (DFC295; Leica, Germany) and analyzed with ImageJ software (National Institute of Health, USA).

Immune Fluorescence Staining in Liver Sections

Fluorescence Immunohistochemistry:

Liver tissue sections (5 m thick) were deparaffinized, rehydrated and boiled for 10 minutes in sodium citrate buffer (10 mM, pH 6.0). Sections were washed in PBS, incubated in 2 mg/ml glycine for 10 minutes to quench auto-fluorescence caused by free aldehydes and then blocked for 1 hour at room temperature with 1% bovine serum albumin (BSA) in PBS. The sections were then incubated overnight at 4° C. with the following primary antibodies diluted in PBS with 1% BSA: mouse monoclonal anti-human CCL24 (1:100 dilution; Chemomab, Tel Aviv, Israel) and rat polyclonal anti-human CCR3 (; 1:50 dilution; catalogue number MAB155-100; R&D Systems). The day after, the slides were washed three times in PBS and incubated for 45 minutes at room temperature in the dark with Alexa Fluor-488 conjugated goat anti-mouse IgG or Rhodamine Red-X-conjugated goat anti-rat IgG (Invitrogen, San Diego, Calif., USA) diluted 1:200 in PBS with 1% BSA, as secondary antibodies. Irrelevant isotype-matched and concentration-matched mouse and rat IgG (Sigma-Aldrich, St. Louis, Mo., USA) were used as negative controls. Cross-reactivity of secondary antibodies was tested in control experiments in which primary antibodies were omitted. Nuclei were counterstained with 4', 6-diamidino-2-phenylindole (DAPI; Chemicon International, Temecula, Calif., USA). Liver sections were then mounted with an antifade aqueous mounting medium (Biomeda Gel Mount; Electron Microscopy Sciences, Foster City, Calif., USA) and examined with a Leica DM4000 B microscope equipped with fully automated fluorescence axes (Leica Microsystems, Mannheim, Germany). Fluorescence images were captured with a Leica DFC310 FX 1.4-megapixel digital color camera equipped with the Leica software application suite LAS V3.8 (Leica Microsystems).

Measurement of ALT, AST, Alkaline Phosphatase and Bilirubin:

Blood was centrifuged and sera was obtained. Levels of ALT, AST, Alkaline phosphatase and Bilirubin were measured in sera using COBAS 6000.

Generating Knock Out Mice to CCL24

CCL24 knockout (KO) C57BL/6 mice were generated by CRISPR/Cas9-mediated genome engineering. Cas9 mRNA and gRNA for CCL24 were generated by in vitro transcription and then injected into fertilized eggs for KO mouse production. The founder mice were genotyped by PCR followed by DNA sequencing analysis. The positive founders were bred to the next generation which was genotyped by PCR and DNA sequencing analysis. Additional breeding was conducted and double knock out mice for CCL24 were established as revealed by PCR genotyping. Potential off-target sites that have been identified by PCR and sequence analysis were tested and verified as negative.

CCL24 Knockout Mice with Inducible NASH

CCL24 knock out on C57BL background were generated using CRISPER technology as described above. WT C57BL mice or CCL24 knock out mice at age 6 weeks were fed with methionine choline deficient diet for 4 weeks. After 4 weeks, mice were sacrificed and their livers were harvested for histology and collagen measurement (Sircol™). Blood was collected from the Orbital Sinus for assessment of ALT, Alkaline phosphatase and bilirubin.

In Vivo MCD Diet Induced NASH Model

Female C57BL mice at age 6 weeks were fed with methionine choline deficient (MCD) diet for 6 weeks. Starting ten days following diet initiation, mice were treated twice weekly with 5 mg/kg, 0.5 mg/kg or 0.05 mg/kg in 100

µl intraperitoneal injections of CM-101 or PBS. The treatment with CM-101 commenced after onset of disease symptoms.

Mice were sacrificed after 6 weeks, blood was collected from the Orbital Sinus (centrifuged to obtain serum at 4° C. (3000×g) as described below for the ANIT model) for assessment of aspartate amino transferase (AST), alanine aminotransferase (ALT), Alkaline phosphatase and bilirubin levels. In addition, the liver was harvested for histopathology analysis and subjected to paraffin embedding for hematoxylin eosin (H&E staining). Frozen tissues were used for collagen assay (Sircol™) and assessment of liver CCL24 level.

STAM Mouse Model for NASH Induction

A single subcutaneous injection of 200 µg streptozotocin (STZ, Sigma-Aldrich, USA) solution was administrated 2 days after birth to male C57BL/6 mice followed by a high fat diet (HFD, 57 kcal % fat, Cat #HFD32, CLEA Japan, Japan) from the age of 4 weeks. Control IgG and CM101 (7.5 mg/kg) was administered intraperitoneally in a volume of 10 l/kg twice weekly from 6 to 9 weeks of age.

Alpha-Naphthylisothiocyanate (ANIT)-Induced Cholestasis Mouse Model

Female C57BL mice were treated on day 1 with ANIT (dissolved in oil, 60 mg/kg) by oral gavage (10 ml/kg). The control group was administered with olive oil by oral gavage. CM101 or vehicle was administered IP, 5 mg/kg once to the ANIT treated groups. 48 hours after ANIT administration, mice were anesthetized with isoflurane and euthanized. Blood samples were collected and centrifuged to obtain serum at 4° C. (3000×g) to test: ALT, AST, ALP, BILLIRUBIN (the chemistry panel). In addition, livers were collected in formalin and embedded in paraffin for hematoxylin and eosin (H&E) staining.

Cholestasis Induced by Bile Duct Ligation

Male Sprague Dawley (SD) rats (8 weeks of age) were anesthetized with Ketamine/Xylazine (Ket 50 mg/kg and Xyl 10 mg/kg) intraperitoneally. The operation site of the abdominal wall was shaved and cleaned and the liver was gently retracted to reveal the bile duct for ligation. Control sham operated animals underwent same procedure with no ligation. From day 0 (day of ligation), rats were administrated twice weekly with intravenous injection of PBS or HCM101 10 mg/kg in a volume of 10 ml/kg. The experiment was terminated by sacrificing the experimental animals after 14 days.

Thioacetamide (TAA) Induced Liver Fibrosis Model in Rats

For disease induction, 7-9 weeks old male Wistar rats were injected intraperitoneally with thioacetamide (250 mg/kg) (Sigma, Cat #172502), twice a week for 8 weeks. HCM101 treated animals (2.5 mg/kg) received intravenous injections of antibody twice weekly from week 4.

Biacore

The affinity constant of HCM101 was evaluated using Biacore T200. This method uses Surface Plasmon Resonance (SPR) electro-optical phenomenon to measure the binding constants and on/off rates between binding partners. HCM101 was immobilized on a surface of a CM-1 chip, and a solution of eotaxin 1 (CCL11)/MCP3 (CCL7) was passed over the surface. The changes in SPR angle were measured and enabled to determine the KD (equilibrium dissociation constant).

DiscoverX β-Arrestin PathHunter and cAMP Hunter™ eXpress CCR5 Assay

To asses G-protein coupled receptor (GPCR) activation following ligand binding the cAMP Hunter™ and β-arrestin PathHunter assay kits (DiscoverX, Fremont, United States) were used according to manufacturer's protocol. Briefly, in the PathHunter GPCR β-Arrestin assay, CHO β-Arrestin CCR3 cells that were engineered to co-express the Pro-Link™ (PK) tagged CCR3 and the Enzyme Acceptor (EA) tagged β-Arrestin were plated in a 96-well plate. To induce chemokine receptor activation cells were exposed to elevated (0, 7.8, 15.6, 31.25, 62.5, 125, 500 and 2000 nM) levels of CCL24. HCM101 inhibitory effect was assessed at a constant CCL24 concentration of 80 nM with elevated antibody concentrations of 5, 15, 45 and 135 µg/ml. Recruitment of β-Arrestin-EA induced by activation of the CCR3-PK receptor results in complementation of the two β-galactosidase enzyme fragments (EA and PK). PathHunter Detection Reagent Substrate is then added to cells for a 60 min incubation period, RT, dark, to enable β-galactosidase enzymatic hydrolysis of the substrate. The generated chemiluminescent signal was assessed by Veritas™ Microplate Luminometer (Turner BioSystems Inc.). For assessment of CCR5 activation, the cAMP Hunter™ system was used. cAMP Hunter™ eXpress CCR5 CHO-K1 Gi cells are designed to detect changes in intracellular cAMP levels in response to agonist stimulation of the receptor. Cells are plated in a 96 well plate and incubated overnight. Cells are exposed to elevated concentration of agonist (0.15625, 0.3125, 0.625, 1.25, 2.5 and 5 µM mip-1α or CCL24) and incubated with cAMP Working Detection Solution for 1 h at the dark. After adding cAMP SolutionA an additional 3 h incubation period is performed before chemiluminescent signal is assessed. To evaluate HCM101 inhibition a constant 100 nM of CCL24 was added with elevated levels of HCM101 (1, 2, 7, 20 and 60 µg/ml).

Measurement of Collagen Content

Soluble collagen was quantified using the Sircol soluble collagen assay (Biocolor, Belfast, UK). Liver samples were obtained from the mice treated with either CM101 (5, 20 or 100 µg/ml), IgG or PBS. The samples were extracted into acid-pepsin solution. The samples were analyzed for collagen content according to the manufacturer's protocol. Briefly, 100 µl of sample was added to 1 ml of the colorimetric reagent (the dye SR in picric acid) and agitated for 30 min followed by centrifugation at 10,000 g for 10 min. The SR dye was released from the pellet with alkali reagent (1 N NaOH) and spectrophotometric readings were taken at 555 nm on a microplate reader.

SMA-α Measurement in Activated Human Hepatic Stellate Cells

Hepatic stellate cells were cultured for 24 hours in serum free DMEM medium. Baseline cell sample was obtained on day 0 for basal measurement of SMA-α.

Cells were incubated for 48 hours with 1% NAFLD patient's serum containing either high or low level of CCL24, as previously measure by ELISA, with or without HCM101 (5 µg/ml). Following 48 hours, cells were centrifuged and stained for intracellular SMA-α fluorescent detection using a commercial kit (How Cytometry Fixation & Permeabilization Buffer Kit I, R&Dsystems; Anti-Human alpha-Smooth Muscle Actin PE, R&Dsystems). Fluorescent signal was measured by FACS (Galius) and analysis was performed using Kaluza Software.

A-SMA Staining in Liver Sections

Sections were cut from frozen liver tissues embedded in O.C.T., fixed in acetone and treated with 0.03% H2O2 for 5 minutes to block endogenous peroxidase activity. Sections were incubated with anti-α-SMA antibody (Abcam, USA diluted 1:200) at RT for 1 hour. After incubation with secondary antibody (HRP-Goat anti-rabbit) enzyme-substrate reactions were performed using 3, 3'-diaminobenzidine/H2O2 solution (Nichirei Bioscience Inc.). Bright field images of α-SMA-positive areas were captured around the central vein using a digital camera (DFC295; Leica, Germany) at 200-fold magnification, and positive areas in 40 fields/section were measured using ImageJ software.

Figure 1B:
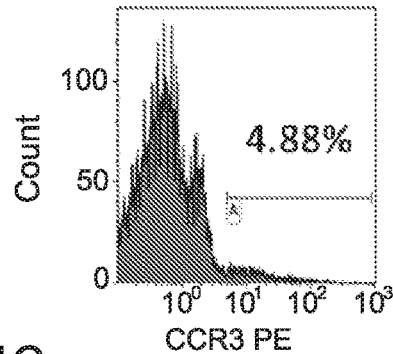
FIG. 1B-1M are FACS images showing representative CCR3 expression on human PBMCs from NAFLD patients compared to healthy control.
Figure 1E:
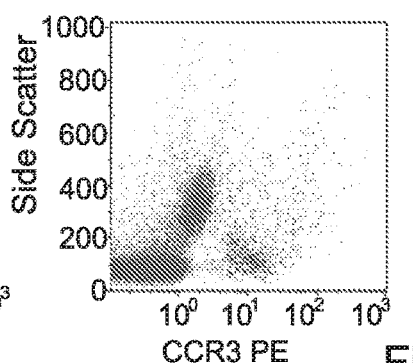
Figure 1C:
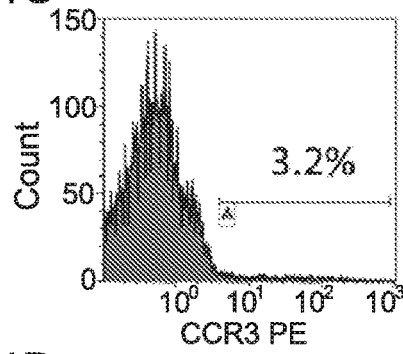
Figure 1F:
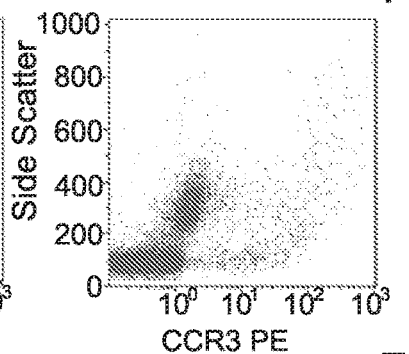
Figure 1D:
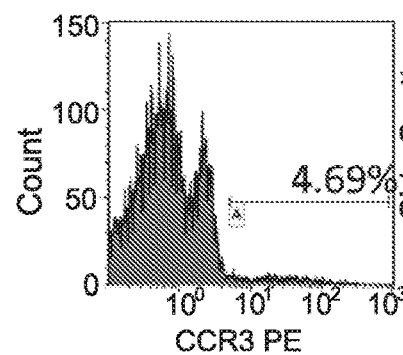
Figure 1G:
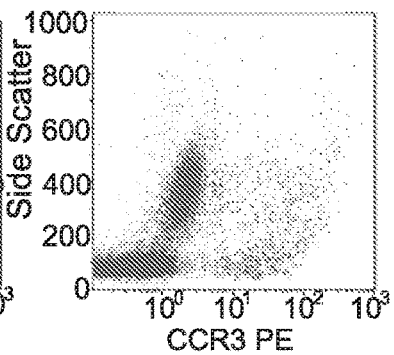
Figure 1H:
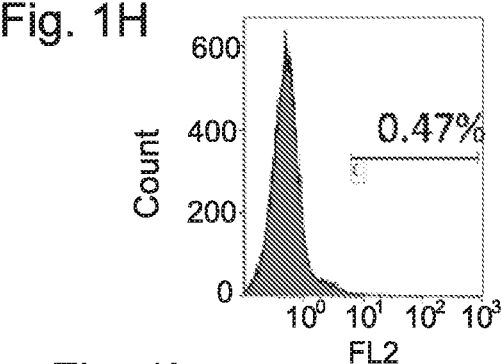
Figure 1K:
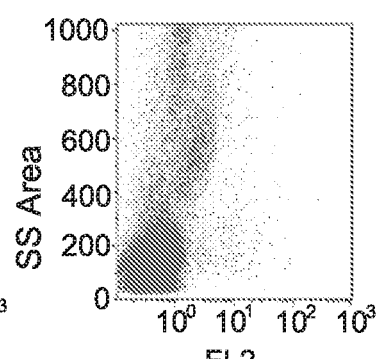
Figure 1I:
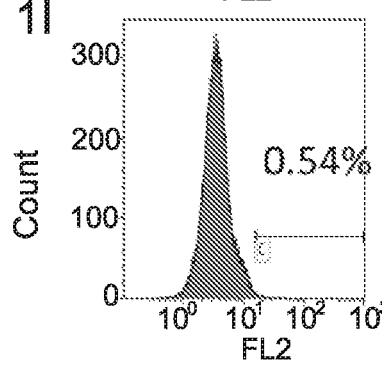
Figure 1L:
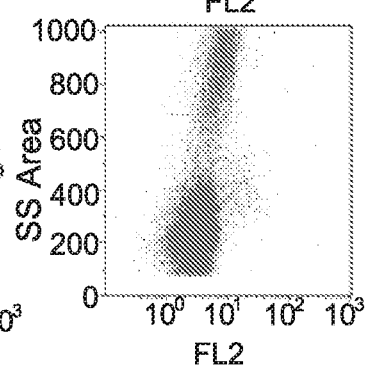
Figure 1J:
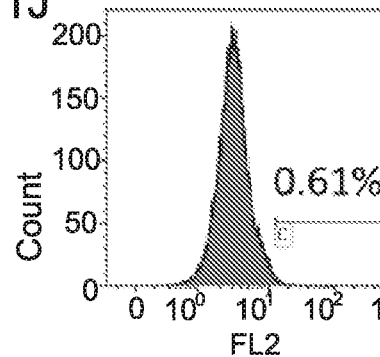
Figure 1M:
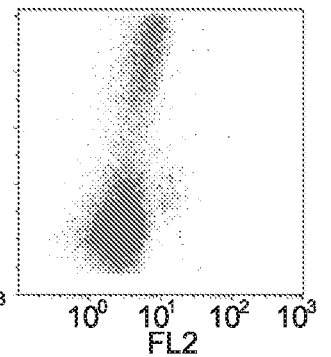
Figure 1N:
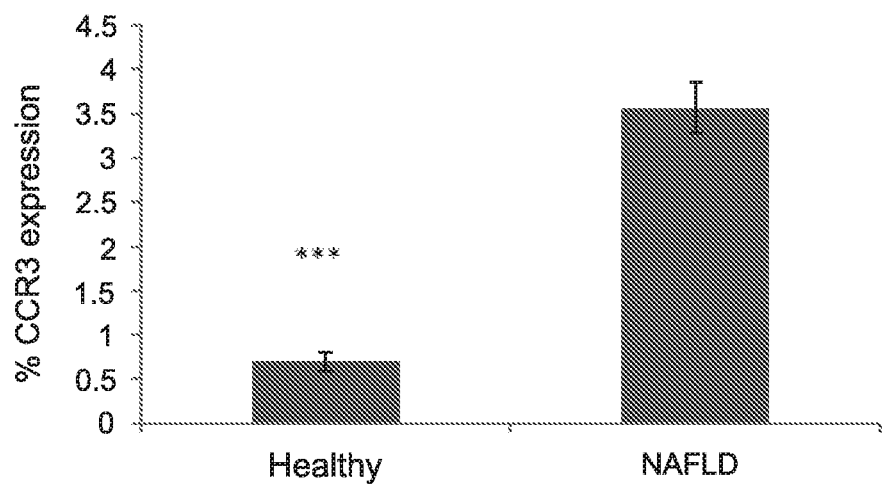
FIG. 1N is a graph showing the expression of CCR3 in peripheral blood mononuclear cells from 10 NAFLD patients compared with control, as measured by FACS. ***pv≤0.005

Example 1: Elevated Levels of CCL24 are Found in Both Serum and Liver Biopsies of Patients with NASH and NAFLD To examine the potential involvement of CCL24 in NASH, the levels of CCL24 were assessed in the serum of NAFLD patients as compared to healthy subjects. The results indicated an increase of 2 fold in CCL24 (pv≤0.01) in patients with high FIB 4 score and 1.5 fold in in patients with low FIB 4 score (pv≤0.05) as shown in FIG. 1A. A high fibrotic score is an indication for a higher probability for NASH. In accordance, elevated levels of CCL24 in NAFLD patients were also associated with elevated CCR3 expression on PBMC taken from blood samples of either healthy or NAFLD patients (FIG. 1B-1N). The CCR3 levels were measured using FACS analysis of isolated PBMC stained with anti CCR3 antibodies. As can be seen in FIG. 1B-1C 4.88%, 3.2% or 4.69% of the PBMC of NAFLD patients showed CCR3 expression, as compared with 0.47%, 0.54% or 0.61% in PBMC of healthy patients.

Figure 2A:
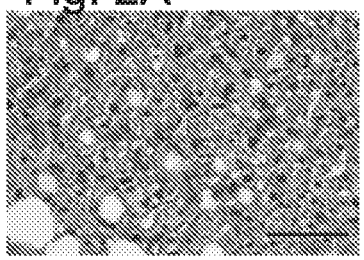
FIG. 2A-2G are photographs showing representative appearance of human liver biopsies obtained from NASH patients stained with anti CCL24 antibodies (i.e. the murine CCL24 mAb CM101) or anti CCR3 antibodies.
Figure 2B:
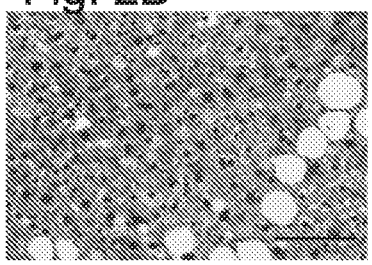
Figure 2C:
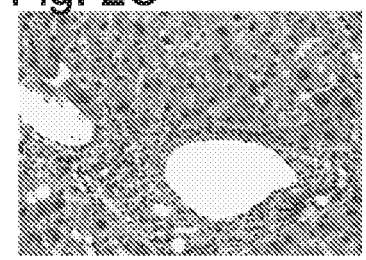
Figure 2D:
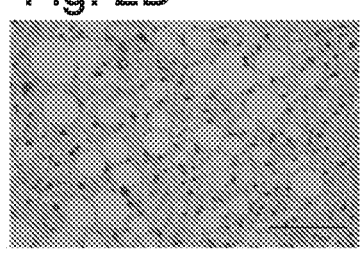
Figure 2E:
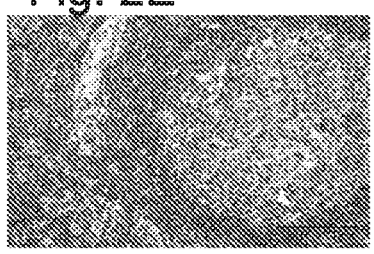
Figure 2F:
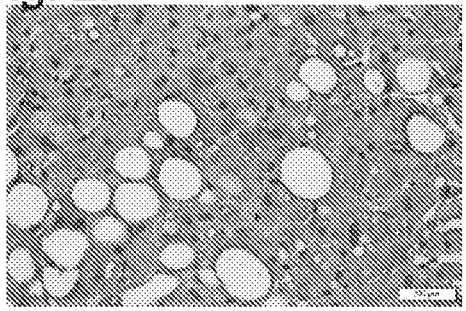
Figure 2G:
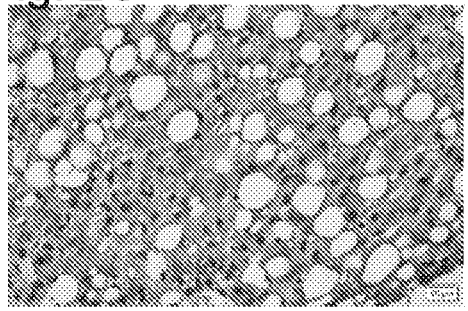

In addition, a significantly elevated expression of CCL24 was detected in liver biopsies taken from NASH patients (FIG. 2A-C), while no CCL24 expression was detected in healthy livers (FIG. 2D-2E). FIGS. 2F and 2G show that the CCL24 associated receptor CCR3, is also expressed in the liver. Without wishing to be bound by theory, it appears that CCL24 may have an important role in the progression of NASH. In the next example, the effect of anti CCL24 monoclonal antibodies was assessed in in vivo models of liver disease.

Figure 3A:
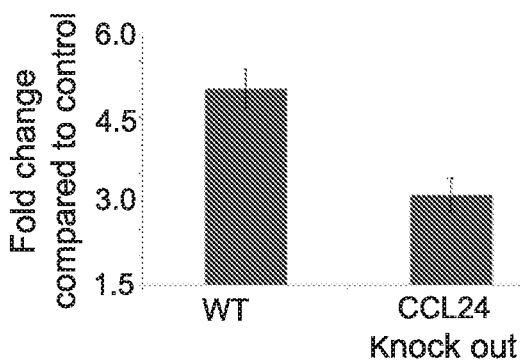
FIG. 3A is a graph showing the level of the liver enzyme ALT in wild type (WT) mice in comparison with CCL24 knock out mice.
Figure 3B:
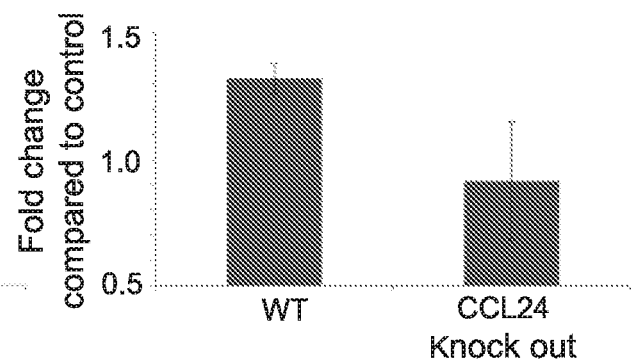
FIG. 3B is a graph showing the level of the liver enzyme ALP in wild type mice in comparison with CCL24 knock out mice.
Figure 3C:
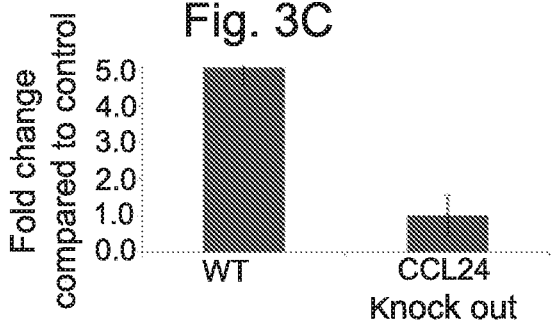
FIG. 3C is a graph showing the Bilirubin level in wild type mice in comparison with CCL24 knock out mice.

Example 2: Characterization of Liver Functions in MCD Induced NASH Model in CCL24 Knockout Mice CCL24 knockout (KO) mice were produced as described in the Materials and Methods section. NASH was induced in these mice by feeding the CCL24 KO C57BL mice with MCD. NASH was also induced in a control group with a normal genetic C57BL background (referred to as "wild-type"). Various liver characteristics were tested to demonstrate the effect of the CCL24 knockout on disease progression. As shown in FIG. 3, ALT (FIG. 3A), ALP (FIG. 3B) and bilirubin (FIG. 3C) serum levels were significantly higher in wildtype mice than in the CCL24 knockout mice. Similarly, as shown in FIG. 3D collagen concentration in the liver was much higher in wildtype mice than in the CCL24 knockout mice. And as shown in FIG. 3E, the NAS score (NAFLD Activity Score), a system of scoring the features of nonalcoholic fatty liver disease that was developed as a tool to measure changes in NAFLD during therapeutic trials, was much lower in the knockout mice than in the wildtype. Without wishing to be bound by theory, the results clearly demonstrate the importance of CCL24 in NASH development. FIGS. 3F to 3K show representative HE stained liver sections.

Example 3: Treatment with the Anti CCL24 mAb CM101 Reduces NASH Features in a Mouse Model The effect of inhibition of CCL24 on NASH progression was further assessed using the murine anti CCL24 antibody CM101. Murine CM101 is a mouse monoclonal antibody directed against human CCL24 (WO2010/086854). In order to evaluate the effect of treatment with CM101 on NASH, methionine choline deficient (MCD) diet was used to induce NASH in a murine model.

NASH was induced by feeding C57BL mice with MCD diet for 6 weeks. A control group was fed with normal chow diet.

CM101 (0.05, 0.5, 5 mg/kg) or PBS were injected intraperitoneally twice weekly to the MCD fed mice from day 10, when disease symptoms are already present. 6 weeks after the onset of the diet, the mice were sacrificed and liver and blood samples were obtained from all groups.

Figure 4A:
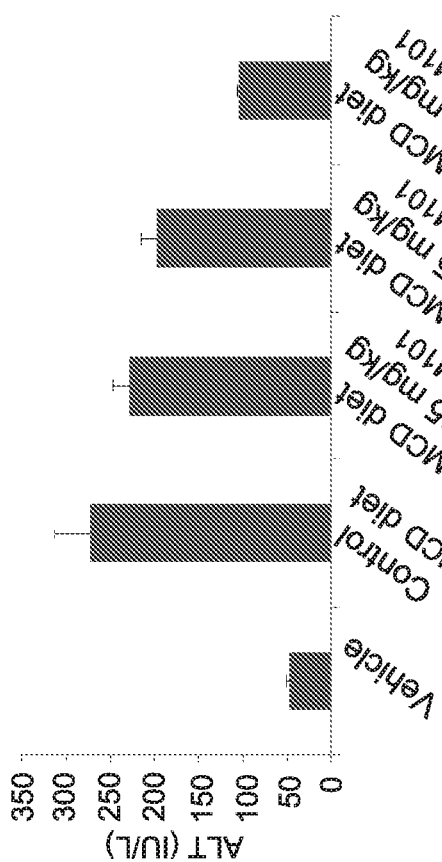
FIGS. 4A-4D are graphs showing levels of AST (FIG. 4A), ALT (FIG. 4B), bilirubin (FIG. 4C) or collagen (FIG. 4D) in mice fed with MCD diet and treated with different concentrations of the anti-CCL24 monoclonal antibody (0.05, 0.5 and 5 mg/kg CM101) or PBS (vehicle).
Figure 4B:
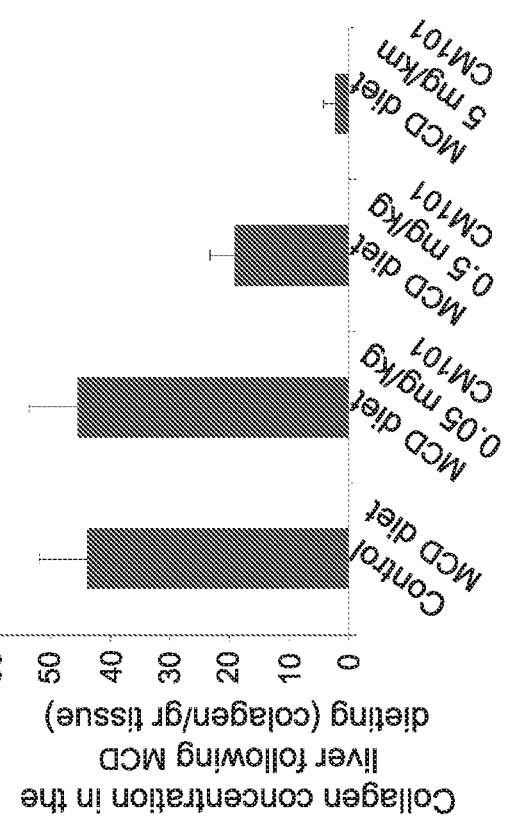
Figure 4C:
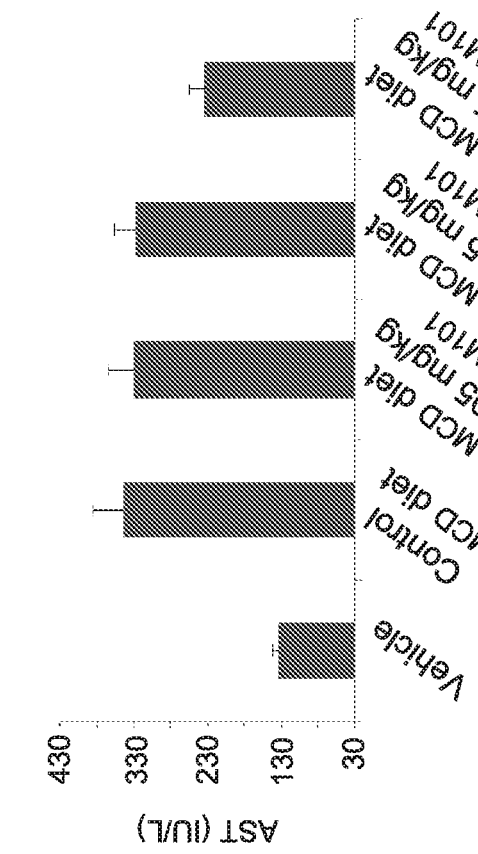
Figure 4D:
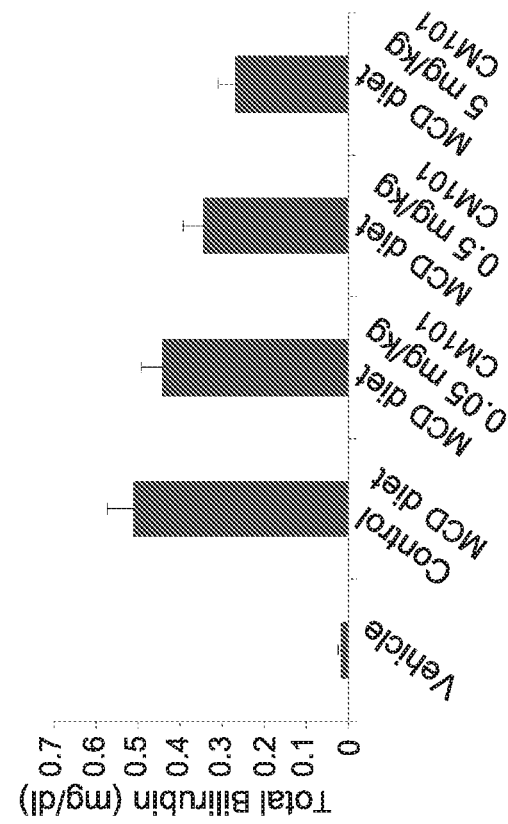

Significant decrease of NASH parameters was observed in mice treated with 5 mg/kg CM-101, compared to those treated with PBS or lower doses. As shown in FIG. 4, 5 mg/kg CM-101 high dose attenuated the increase of all the tested parameters (liver enzymes, liver collagen level and liver histological score). ALT, AST and Bilirubin (FIG. 4A-4C) were reduced significantly ($p<0.05$) in the high dose CM-101 treated group, as compared to PBS treated mice. The effect of CM-101 was also evident in a significant reduction of liver collagen concentration demonstrating 95% reduction of liver collagen in the group treated with 5 mg/kg CM-101, reversing it back to normal basal collagen level (as shown in FIG. 4D). Determination of NAFLD activating score in H&E liver staining (pictures of histological sections in FIG. 4E-4L) revealed a significant reduction from 7 score to 5 score in the group treated with 5 mg/kg CM-101 (FIG. 4M).

Finally, to validate target engagement within the liver, the levels of CCL24 in the liver were evaluated, showing adequate reduction in the protein expression due to treatment with CM101 (FIG. 4N).

Example 4: Amelioration of NAFLD Activity Score and Fibrosis in the STAM Mouse NASH Model by CM101 Treatment The anti-fibrotic and anti-inflammatory effects of CM101 treatment were further evaluated in the STAM mouse model for NASH. STAM mice represent a model that closely mimics the pathophysiological processes of NASH development in humans, exhibiting all stages of disease from steatosis, through NASH to fibrosis and hepatic carcinoma. These animals receive a single subcutaneous injection of streptozotocin 2 days after birth followed by a high fat diet that induces NASH resembling liver damage.

Figure 5N:
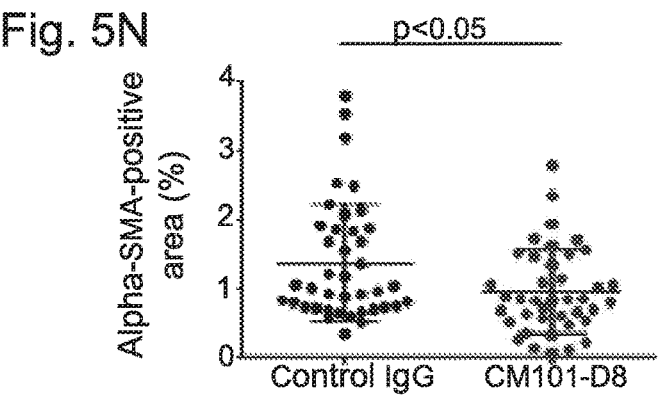
Figure 11A:
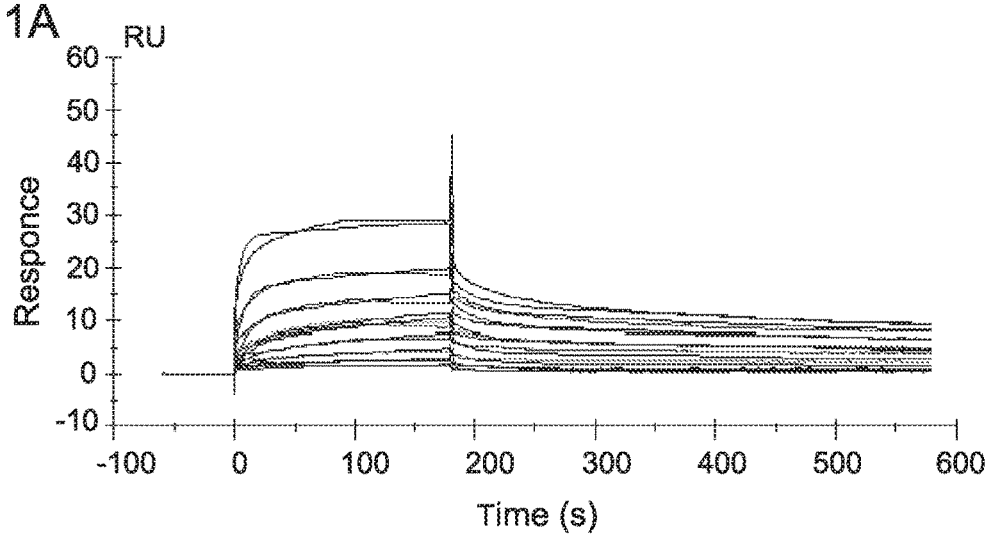
FIG. 11A shows representative Biacore binding curves of CCL11 (Eotaxin 1) to HCM101.
Figure 11B:
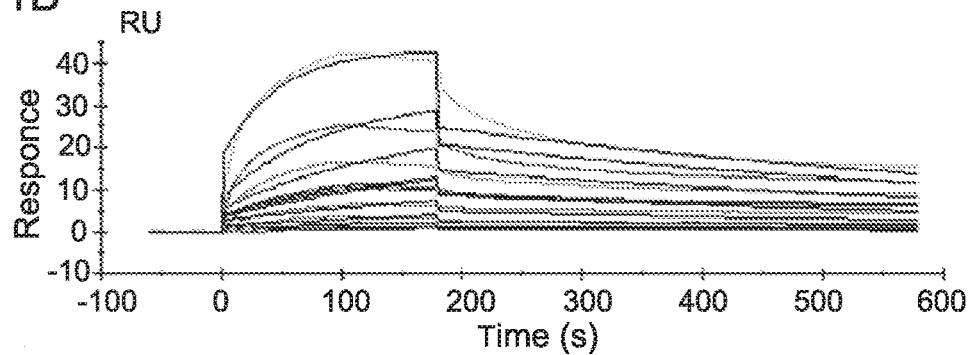
FIG. 11B shows representative Biacore binding curves of CCL7 (MCP3) to HCM101.

Histopathological analysis showed that administration of 7.5 mg/kg of CM101 to STAM mice reduced liver damage assessed by H&E staining (FIGS. 5A-5D) and significantly attenuated the NAFLD activity score (NAS score) by 32% compared to the control IgG treated group (FIG. 5E). This effect predominantly resulted from substantial improvement in hepatocyte ballooning that decreased by 65% (FIG. 5F). CM101 significantly reduced accumulation of liver collagen and fibrosis demonstrated by decreased Sirius red positive area compared with the control group (FIG. 5G-5K). Alpha-Smooth muscle actin (ca-SMA) that represents activation of liver hepatic stellate cells, responsible for fibrosis establishment and most of the collagen deposition in the liver, was also evaluated in STAM mice. Anti-CCL24 treatment resulted in a significant reduction of α-SMA-positive stained area compared with the Control IgG group (FIG. 5L-5N).

Example 5: CM101 Significantly Reduce Liver Damage and Fibrosis in the Rat TAA Induced Liver Fibrosis Model To determine the specific effect of HCM101 treatment on fibrosis, a rat toxicity (TAA) induced fibrosis model was investigated. Inhibition of CCL24 resulted in reduction of liver damage, indicated by significantly decreased liver enzyme levels compared to untreated controls. Moreover, macroscopic examination of liver injury revealed pronounced amelioration of liver pathology with reduced regenerative nodules and decreased damage (FIG. 6A-6B). Assessment of fibrosis by Sirius staining of liver sections showed an average of 5 fold decrease in collagen deposition and almost 2 fold decrease in inflammation in the HCM101 treated group compared to untreated controls (FIG. 6C). Further evaluation of collagen deposition by Sircol quantification, revealed a significant reduction of 45% in collagen content (FIG. 6D).

Example 6: CCL24 and its Receptor CCR3 are Overexpressed in the Liver and Circulation of PSC Patients CCR3 levels were evaluated on PBMCs from primary sclerosing cholangitis (PSC) and Healthy volunteers (n=10, n=22, respectively) using a commercial anti CCR3 antibody. As shown in FIGS. 7A-7E significant increase of CCR3 levels were found in PSC patients (3.94%±1.35) compared to healthy individuals (0.68%±0.36). CCL24 and CCR3 were assessed in livers of PSC patients using immunofluorescence. As shown in FIGS. 7F-7I, CCL24 and CCR3 levels were significantly overexpressed in immune cells, cholangiocytes and hepatocytes.

Example 7: CM101 Robustly Ameliorates Liver Damage in Experimental Primary Sclerosing Cholangitis (PSC) Model To assess the effect of CM101 in PSC animal model, the rodent cholestasis model induced by ANIT compound was used.

The elevated serum levels of Bilirubin, alkaline phosphatase, ALT and AST that are typical to this disease model were significantly reduced by CM101 treatment in the ANIT-induced cholestatic mice by 87, 47, 33 and 48% respectively (FIG. 8A). In addition, the histopathological effect of CM101 was studied by evaluating hepatic necrosis using H&E staining. It was found that ANIT-induced liver injuries were attenuated by CM101 treatment in mice (FIG. 8B). The effect of treatment with CM101 was further assessed in a second model of cholestasis induced by bile duct ligation in rats. Fibrosis associated with doctoral reaction and liver damage in this model was assessed by Sirius red staining and showed significant reduction of damage in the liver of rats treated with anti CCL24 mAb compared to operated animals with no treatment (FIG. 9A-9B).

Example 8: The Fully Humanized HCM101 Antibody Attenuates Transition of Hepatic Stellate Cells (HSC) to Myofibroblasts In many organs, myofibroblasts play a major role in the scarring process in response to injury. In liver fibrogenesis or cirrhosis, hepatic stellate cells (HSCs) are considered the precursor population (namely, they transdifferentiate) into myofibroblasts.

The myofibroblast is a specialized fibroblast characterized by cytoplasmic stress fibers with alpha smooth muscle actin (αSMA). Since αSMA is a factor that characterizes myofibroblasts, measurements of intracellular αSMA levels can serve as an indicator of transition of hepatic stellate cells (HSC) to myofibroblasts, and hence serves as an indicator of the severity of the liver cells' condition.

In order to measure the effect of an anti CCL24 antibody on CCL24 mediated HSC transition to myoblasts, an HSC cell line was used. The assay was performed using the fully humanized anti CCL24 antibody HCM101 (WO 2015/132790). The cells were incubated for 48 hours at 37° C. in the presence of 1% NAFLD patients' sera with or without humanized HCM101 (5 µg/ml). The level of αSMA was measured by FACS to evaluate cell activation and transition to myofibroblasts (FIG. 10).

Control non-activated cells, namely cells that were not exposed to patient's sera, showed 2.7% SMA positive staining, as measured by intracellular staining and FACS analysis. In hepatic stellate cell cultures activated with serum obtained from a NAFLD patient with high CCL24 levels (3521 pg/ml as measured by ELISA), 34% of the cells were SMA positive cells. When the serum was pre-treated with the humanized anti CCL24 antibody HCM101 (10 µg/ml) for 1 hour in 37° C., only 15% SMA positive cells were present in the culture. Interestingly, only 23% SMA positive cells were present in hepatic stellate cells activated with serum obtained from a NAFLD patient with low CCL24 levels (193 pg/ml). When the serum was pre-treated with the humanized anti CCL24 antibody HCM101 (10 µg/ml) only 19% SMA positive cells were present in the culture.

The results show that elevated expression of αSMA was more robust in HSC treated with NAFLD serum that contained high levels of CCL24, than sera that contained lower levels of the chemokine.

Furthermore, the humanized anti CCL24 antibody HCM101, caused a 50% reduction in expression of αSMA in cultures that were activated by exposure to sera containing high CCL24 levels. Without wishing to be bound by theory, it appears that the anti CCL24 antibody attenuated CCL24-mediated transition of hepatic stellate cells (HSC) to myofibroblasts.

Example 9: Affinity and Binding Specificity of HCM101

Biacore, an SPR based technology was used in order to examine the binding affinity of HCM101, generated by CHO cells, to other, non-CCL24 chemokines. Considerable binding of the antibody to Eotaxin 1 (CCL11) and MCP3 (CCL7) was demonstrated by Biacore (FIGS. 10A and 10B, respectively) revealing an affinity constant of 30 nM and 130 nM, respectively.

Example 10: HCM101 Inhibits Both CCR3 and CCR5 Chemokine Receptor Activation After establishing that HCM101 can also bind CCL11 and CCL7, its effectiveness and potency was further evaluated by assessing the activation potential of CCL24 through possibly binding other chemokine receptors. Towards this aim, the DiscoverX chemokine activation system was used. This system utilizes engineered cells that produce a luminescence signal induced by receptor activation. Two different activation systems of DiscoverX cells were used, a CCR3 β-Arrestin assay that produces a signal when CCR3 is activated by recruitment of engineered β-Arrestin, and a CCR5 cAMP assay that gives a signal proportional to intracellular concentrations of cAMP that is reduced at the onset of receptor activation.

Figure 12A:
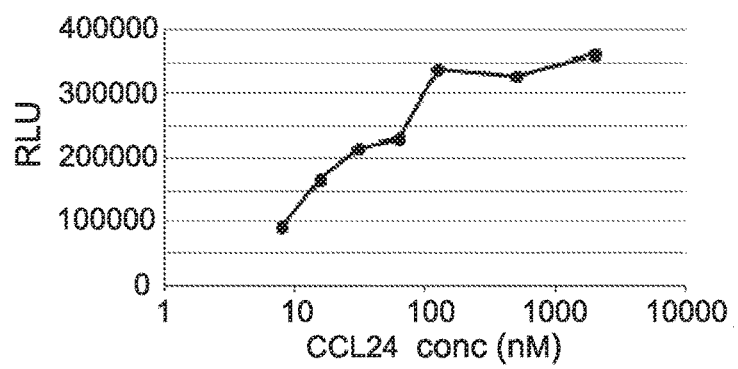
FIG. 12A-12F show chemokine receptor activation in the DiscoverX system indicated by either β-arrestin recruitment or cAMP inhibition.
Figure 12B:
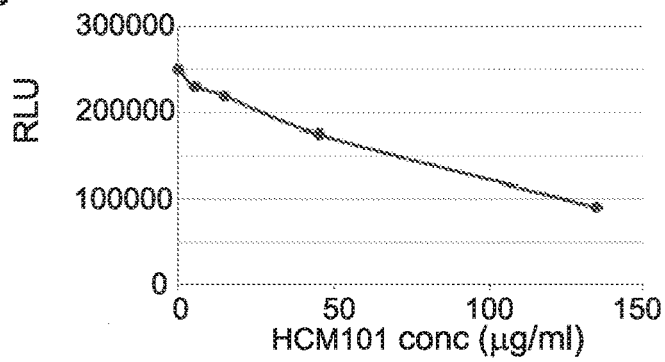

CCL24 induced a dose dependent response in the CCR3 β-Arrestin system, with pronounced activation of the receptor by ligand (CCL24) concentrations ranging from 7-2000 nM (FIG. 12A). Adding HCM101 at different concentrations resulted in a significant dose dependent inhibition of CCR3 activation by CCL24 (FIG. 12B) with up to 70% reduction in activity.

Figure 12C:
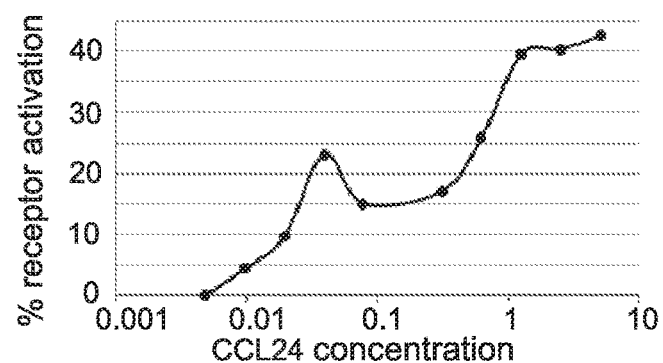
Figure 12D:
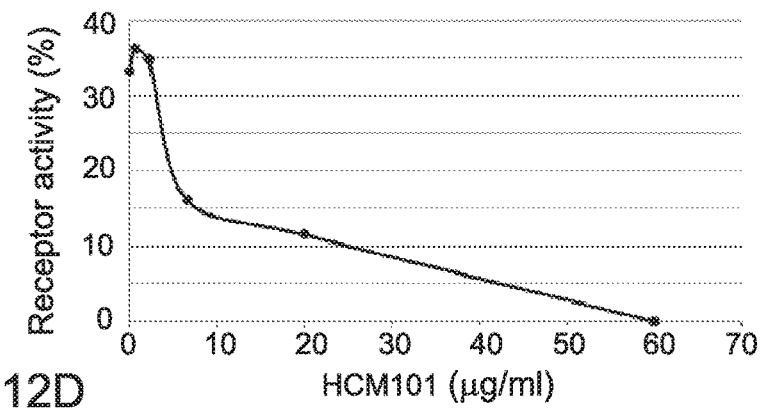
Figure 12E:
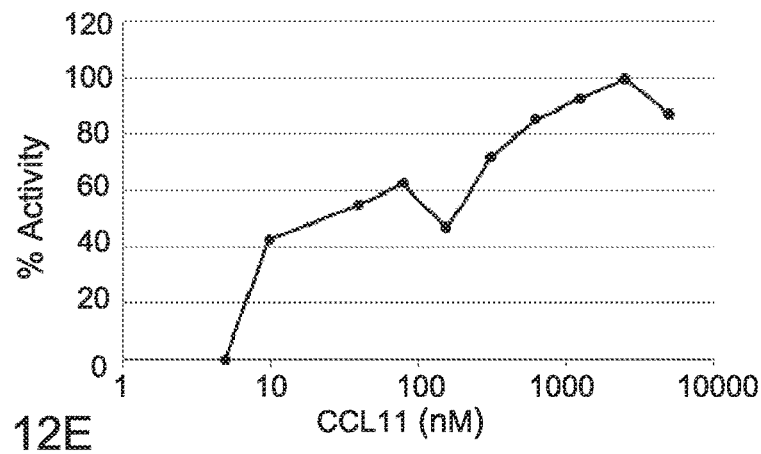
Figure 12F:
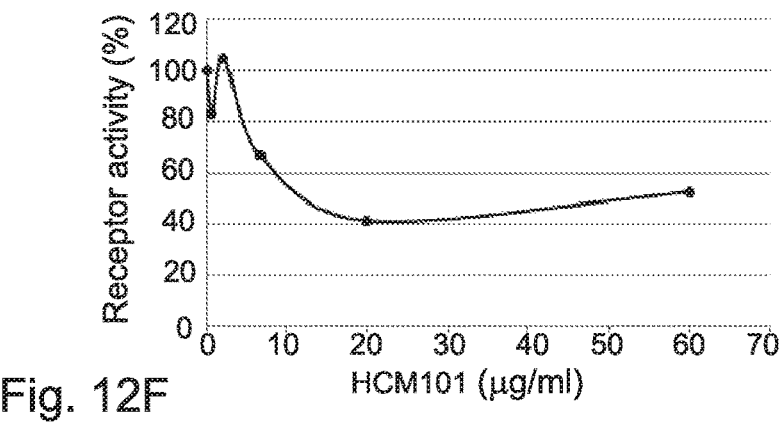

To assess the ability of CCL24 to activate cells through additional chemokine receptors, a second DiscoverX system was used indicating activation of the CCR5 chemokine receptor. As a control, mip-1α, a well-known and established CCR5 ligand, was tested for its ability to induce receptor activation, represented by decreased intracellular levels of cAMP. Indeed a dose dependent reduction in cAMP was observed in different concentrations of mip-1α (data not shown). Treating these CCR5-cAMP cells with CCL24 resulted in a dose dependent activation of the receptor evident from decreased cAMP levels at concentrations ranging from 0.15-5 μM (FIG. 12C). HCM101 supplementation opposed this effect, increasing cAMP intracellular levels at different (7-60 μg/ml) antibody concentrations, which is indicative of reduced receptor activation up to 70% inhibition of CCR5 activation (FIG. 12D). The CCR5 cAMP system was further used to examine the effect of HCM101 on CCL11. Administration of CCL11 at concentrations ranging from 4 nM to 5 μM caused a dose dependent activation of CCR5. Administration of HCM101 attenuated the CCL11-induced CCR5 activation by up to 60% (FIGS. 12E and 12F).

Example 11: Effect of CM101 on Autoimmune Hepatitis

Autoimmune hepatitis (AIH) is a chronic inflammatory liver disease associated with interface hepatitis, raised plasma liver enzymes, the presence of autoantibodies and regulatory T-cell (Tregs) dysfunction. Concanavalin (Con)-A induced hepatitis in rats is an animal model for studying AIH and for evaluating potential therapeutics.

For induction of acute hepatitis in a rat model, concanavalin A (ConA) dissolved in 300 μl PBS is administered to each rat via the tail vein in doses of 5 mg/kg. Control rats receive 300 μl of PBS alone. Animals receive subcutaneously HCM101 2.5 mg/kg or control IgG on day 0. Animals are sacrificed 48 h after Con A administration. AST, ALT, TNF-α, IFN-γ and CCL24 levels are assessed. Histopathology analysis of liver leukocytes infiltration, Hepatic necrosis and liver fibrosis are assessed as well.

For induction of chronic hepatitis, 10 mg/kg Con A are administered IV once weekly for 12 weeks. 2.5 mg/kg CM101 or IgG are administered subcutaneously from week 2 to week 12. Control group receives PBS instead of concanavalin A (ConA). Liver enzymes (e.g. AST, ALT), liver Histological analyses for necrosis and inflammation fibrosis and alpha-SMA are assessed.

---

The invention claimed is:

1. A method of treating hepatic pathologies comprising administering to a patient in need thereof a therapeutically acceptable amount of an isolated anti CCL24 (eotaxin 2) antibody, or any antigen-binding fragment thereof or a pharmaceutical composition comprising said isolated antibody, wherein said antibody is a fully humanized antibody comprising six CDR sequences as denoted by SEQ ID Nos 1-6, and a heavy chain variable region having at least 90% sequence homology to SEQ ID NO:7 and a light chain variable region having at least 90% sequence homology to SEQ ID NO: 8, and wherein said hepatic pathologies are intrahepatic cholestatic liver diseases.

2. The method of claim 1, wherein said antibody is a fully humanized antibody comprising the heavy chain variable region denoted by SEQ ID NO:7 or a variant thereof and the light chain variable region denoted by SEQ ID NO: 8.

3. The method of claim 1, wherein said antibody is administered in combination with at least one additional therapeutic agent.

4. The method of claim 1, wherein the intrahepatic cholestatic liver diseases are selected from the group consisting of primary sclerosing cholangitis (PSC), primary biliary cirrhosis (PBC), and cholangiocarcinoma resulting from PSC.

* * * * *

SEQUENCE LISTING

<160> NUMBER OF SEQ ID NOS: 12

<210> SEQ ID NO 1
<211> LENGTH: 5
<212> TYPE: PRT
<213> ORGANISM: Homo sapiens

<400> SEQUENCE: 1

Asn Ser Gly Met Asn
1               5

<210> SEQ ID NO 2
<211> LENGTH: 17
<212> TYPE: PRT
<213> ORGANISM: Homo sapiens

<400> SEQUENCE: 2

Trp Ile Asn Thr Tyr Asn Gly Glu Pro Thr Tyr Thr Asp Asp Phe Lys
1               5                   10                  15

Gly

<210> SEQ ID NO 3
<211> LENGTH: 11
<212> TYPE: PRT
<213> ORGANISM: Homo sapiens

<400> SEQUENCE: 3

His Ser Tyr Gly Ser Ser Tyr Ala Met Asp Asn
1               5                   10

<210> SEQ ID NO 4
<211> LENGTH: 15
<212> TYPE: PRT
<213> ORGANISM: Homo sapiens

<400> SEQUENCE: 4

Lys Ala Ser Gln Ser Val Asp Tyr Asp Gly Asp Ser Tyr Met Asn
1               5                   10                  15

<210> SEQ ID NO 5
<211> LENGTH: 7
<212> TYPE: PRT
<213> ORGANISM: Homo sapiens

<400> SEQUENCE: 5

Val Ala Ser Asn Leu Lys Ser
1               5

<210> SEQ ID NO 6
<211> LENGTH: 9
<212> TYPE: PRT
<213> ORGANISM: Homo sapiens

<400> SEQUENCE: 6

Gln Gln Ser Asn Glu Glu Pro Trp Thr
1               5

<210> SEQ ID NO 7
<211> LENGTH: 120
<212> TYPE: PRT
<213> ORGANISM: Homo sapiens

<400> SEQUENCE: 7

Gln Ile Gln Leu Val Gln Ser Gly Pro Glu Leu Lys Lys Pro Gly Ala
1               5                   10                  15

Ser Val Lys Val Ser Cys Arg Ala Ser Gly Tyr Pro Phe Thr Asn Ser
            20                  25                  30

Gly Met Asn Trp Val Lys Gln Ala Pro Gly Lys Gly Leu Lys Trp Met
        35                  40                  45

Gly Trp Ile Asn Thr Tyr Asn Gly Glu Pro Thr Tyr Thr Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Arg Asn Glu Asp Thr Ala Thr Tyr Phe Cys
                85                  90                  95

Ala Ser His Ser Tyr Gly Ser Ser Tyr Ala Met Asp Asn Trp Gly Gln
            100                 105                 110

Gly Thr Ser Val Thr Val Ser Ser
        115                 120

<210> SEQ ID NO 8
<211> LENGTH: 111
<212> TYPE: PRT
<213> ORGANISM: Homo sapiens

<400> SEQUENCE: 8

Asp Ile Val Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Val Ala Ser Asn Leu Lys Ser Gly Ile Pro Ala
    50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Asn
                 85                  90                  95

Glu Glu Pro Trp Thr Phe Gly Gly Gly Thr Lys Val Glu Ile Lys
            100                 105                 110

<210> SEQ ID NO 9
<211> LENGTH: 426
<212> TYPE: DNA
<213> ORGANISM: Mus musculus
<220> FEATURE:
<221> NAME/KEY: misc_feature
<222> LOCATION: (11)..(11)
<223> OTHER INFORMATION: n is a, c, g, t or u
<220> FEATURE:
<221> NAME/KEY: misc_feature
<222> LOCATION: (19)..(19)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (33)..(33)
<223> OTHER INFORMATION: n is a, c, g, t or u
<220> FEATURE:
<221> NAME/KEY: misc_feature
<222> LOCATION: (39)..(40)
<223> OTHER INFORMATION: n is a, c, g, t or u
<220> FEATURE:
<221> NAME/KEY: misc_feature
<222> LOCATION: (42)..(42)
<223> OTHER INFORMATION: n is a, c, g, t or u
<220> FEATURE:
<221> NAME/KEY: misc_feature
<222> LOCATION: (386)..(386)
<223> OTHER INFORMATION: n is a, c, g, t or u
<220> FEATURE:
<221> NAME/KEY: misc_feature
<222> LOCATION: (422)..(422)
<223> OTHER INFORMATION: n is a, c, g, t or u

<400> SEQUENCE: 9
gggcagcaga nccggggcng nggatagaca gangggggnn gncgttttgg ctgaggagac    60
ggtgactgag gttccttgac cccagttgtc catagcgtag ctactaccgt aggaatgact   120
tgcacagaaa tatgtagccg tgtcctcatt tctgaggttg ttgatctgca ataggcagt    180 gctggcagag gtttccaaag agagggcaaa ccgtcccttg aagtcatcag tatatgttgg   240
ctctccattg taggtgttga tccagcccat ccactttaaa cccttcctg gagcctgctt    300 tacccagttc attccagagt ttgtgaaggg atacccagaa gccctgcagg agatcttgac   360
tgtgtctcca ggcttcttca gctcangtcc agactgcacc aactggatct gggccatggc   420 cngcta                                                             426

<210> SEQ ID NO 10
<211> LENGTH: 254
<212> TYPE: DNA
<213> ORGANISM: Mus musculus
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t -continued

```
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (49)..(52)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (60)..(61)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (72)..(73)
<223> OTHER INFORMATION: n is a, c, g, or t
<220> FEATURE:
<221> NAME/KEY: misc_feature
<222> LOCATION: (75)..(78)
<223> OTHER INFORMATION: n is a, c, g, or t
<220> FEATURE:
<221> NAME/KEY: misc_feature
<222> LOCATION: (80)..(83)
<223> OTHER INFORMATION: n is a, c, g, or t
<220> FEATURE:
<221> NAME/KEY: misc_feature
<222> LOCATION: (85)..(86)
<223> OTHER INFORMATION: n is a, c, g, or t
<220> FEATURE:
<221> NAME/KEY: misc_feature
<222> LOCATION: (88)..(92)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (100)..(101)
<223> OTHER INFORMATION: n is a, c, g, or t
<220> FEATURE:
<221> NAME/KEY: misc_feature
<222> LOCATION: (107)..(109)
<223> OTHER INFORMATION: n is a, c, g, or t
<220> FEATURE:
<221> NAME/KEY: misc_feature
<222> LOCATION: (111)..(113)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (119)..(121)
<223> OTHER INFORMATION: n is a, c, g, or t
<220> FEATURE:
<221> NAME/KEY: misc_feature
<222> LOCATION: (125)..(126)
```

```
<223> OTHER INFORMATION: n is a, c, g, or t
<220> FEATURE:
<221> NAME/KEY: misc_feature
<222> LOCATION: (131)..(137)
<223> OTHER INFORMATION: n is a, c, g, or t
<220> FEATURE:
<221> NAME/KEY: misc_feature
<222> LOCATION: (139)..(142)
<223> OTHER INFORMATION: n is a, c, g, or t
<220> FEATURE:
<221> NAME/KEY: misc_feature
<222> LOCATION: (145)..(149)
<223> OTHER INFORMATION: n is a, c, g, or t
<220> FEATURE:
<221> NAME/KEY: misc_feature
<222> LOCATION: (153)..(154)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (163)..(166)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (171)..(173)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (180)..(181)
<223> OTHER INFORMATION: n is a, c, g, or t
<220> FEATURE:
<221> NAME/KEY: misc_feature
<222> LOCATION: (183)..(185)
<223> OTHER INFORMATION: n is a, c, g, or t
<220> FEATURE:
<221> NAME/KEY: misc_feature
<222> LOCATION: (187)..(191)
<223> OTHER INFORMATION: n is a, c, g, or t
<220> FEATURE:
<221> NAME/KEY: misc_feature
<222> LOCATION: (196)..(200)
<223> OTHER INFORMATION: n is a, c, g, or t
<220> FEATURE:
<221> NAME/KEY: misc_feature
<222> LOCATION: (202)..(202)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (206)..(206)
<223> OTHER INFORMATION: n is a, c, g, or t
<220> FEATURE:
<221> NAME/KEY: misc_feature
<222> LOCATION: (214)..(214)
```

<223> OTHER INFORMATION: n is a, c, g, or t
<220> FEATURE:
<221> NAME/KEY: misc_feature
<222> LOCATION: (216)..(218)
<223> OTHER INFORMATION: n is a, c, g, or t
<220> FEATURE:
<221> NAME/KEY: misc_feature
<222> LOCATION: (221)..(226)
<223> OTHER INFORMATION: n is a, c, g, or t
<220> FEATURE:
<221> NAME/KEY: misc_feature
<222> LOCATION: (233)..(234)
<223> OTHER INFORMATION: n is a, c, g, or t
<220> FEATURE:
<221> NAME/KEY: misc_feature
<222> LOCATION: (236)..(236)
<223> OTHER INFORMATION: n is a, c, g, or t

<400> SEQUENCE: 10
gggccaatgg nngaggacgc ggatgggggt gtcgnngtgc cttngtcgnn nnctnnttgn      60
ncancntcna cnncnnnnan nnnanngnnn nntgnaanan ngatggnnnt nnncnacann     120
ntggnntcct nnnnnnntnn nntgnnnnng acnncanana cannnncnac nnnatgancn     180
ncnnncnnnn nttgannnnn gncnantatg aacnannnaa nnnnnntacc tgnnangcca     240
ctcacaagac atca                                                       254

<210> SEQ ID NO 11
<211> LENGTH: 360
<212> TYPE: DNA
<213> ORGANISM: Homo sapiens

<400> SEQUENCE: 11
cagatccaat tggtgcagtc tggacctgag ctgaagaagc ctggagcctc agtcaaggtc      60
tcctgcaggg cttctgggta tcccttcaca aactctggaa tgaactgggt aaagcaggct     120
ccaggaaagg gtttaaagtg gatgggctgg atcaacacct acaatggaga gccaacatat     180
actgatgact tcaagggacg gtttgccttc tctttggaaa cctctgccag cactgcctat     240
ttgcagatca acaacctcag aaatgaggac acggctacat atttctgtgc aagtcattcc     300
tacggtagta gctacgctat ggacaactgg ggtcaaggaa cctcagtcac cgtctcctca     360

<210> SEQ ID NO 12
<211> LENGTH: 333
<212> TYPE: DNA
<213> ORGANISM: Homo sapiens

<400> SEQUENCE: 12
gacattgtgc tgacccaatc tccagactct ttggctgtgt ctctagggga gagggccacc      60
atcaactgca aggccagcca aagtgttgat tatgatggtg atagttatat gaactggtac     120
caacagaaac caggacagcc acccaaactc ctcatctatg ttgcatccaa tctaaaatct     180
ggcatcccag ccaggtttag tggcagtggg tctgggacag acttcaccct caccatcagc     240
agcctgcagc ctgaggattt tgcaacctat tactgtcagc aaagtaatga ggaaccgtgg     300
acgttcggtg gaggcaccaa ggtggaaatc aaa                                  333